United States Patent
Anderson et al.

(10) Patent No.: US 9,849,173 B2
(45) Date of Patent: *Dec. 26, 2017

(54) METHODS FOR PREPARING VESICLES AND FORMULATIONS PRODUCED THEREFROM

(75) Inventors: David E. Anderson, Boston, MA (US); Andrei Ogrel, Russell (CA)

(73) Assignee: Variation Biotechnologies Inc., Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/377,365

(22) PCT Filed: Jul. 6, 2010

(86) PCT No.: PCT/US2010/041078
§ 371 (c)(1),
(2), (4) Date: Mar. 6, 2012

(87) PCT Pub. No.: WO2011/005769
PCT Pub. Date: Jan. 13, 2011

(65) Prior Publication Data
US 2012/0156240 A1    Jun. 21, 2012

Related U.S. Application Data

(60) Provisional application No. 61/223,196, filed on Jul. 6, 2009, provisional application No. 61/256,912, filed on Oct. 30, 2009.

(51) Int. Cl.
*A61K 9/127* (2006.01)
*A61K 39/29* (2006.01)
(Continued)

(52) U.S. Cl.
CPC ............ *A61K 39/29* (2013.01); *A61K 9/0019* (2013.01); *A61K 9/127* (2013.01); *A61K 9/1277* (2013.01);
(Continued)

(58) Field of Classification Search
CPC .................................. A61K 8/14; A61K 9/127
See application file for complete search history.

(56) References Cited

U.S. PATENT DOCUMENTS 3,952,097 A    4/1976 Levy
4,024,241 A    5/1977 Levy
(Continued)

FOREIGN PATENT DOCUMENTS

CA     2258907 A1    12/1997
CA     2767392 A1    1/2011
(Continued)

OTHER PUBLICATIONS

F Szoka Jr., D Papahadjopoulos. "Comparative Properties and Methods of Preparation of Lipid Vesicles (Liposomes)." Annual Revies in Biophysics and Bioengineering, vol. 9, 1980, pp. 467-508.*

(Continued)

*Primary Examiner* — Isaac Shomer
(74) *Attorney, Agent, or Firm* — Choate, Hall & Stewart LLP; Brenda Herschbach Jarrell; Rolando Medina

(57) ABSTRACT

The present disclosure provides methods for preparing vesicles. In some embodiments, the methods involve providing a molten mixture of vesicle forming lipids and then adding the molten mixture to an aqueous solution comprising an antigen such that antigen-containing vesicles are formed. In other embodiments, the methods involve providing a lyophilized lipid product and rehydrating the lyophilized lipid product with an aqueous solution comprising an antigen such that antigen-containing vesicles are formed. The lyophilized lipid product is prepared by melting vesicle-forming lipids to produce a molten lipid mixture and then lyophilizing the molten lipid mixture. The present disclosure also provides antigen-containing vesicle formulations prepared using these methods. The present disclosure (Continued)

also provides kits that include a lyophilized lipid product in a first container and an aqueous solution comprising an antigen in a second container.

20 Claims, 4 Drawing Sheets

(51) Int. Cl.
 *A61K 9/00* (2006.01)
 *A61K 39/12* (2006.01)
 *A61K 39/00* (2006.01)
(52) U.S. Cl.
 CPC ............ *A61K 39/12* (2013.01); *A61K 39/292* (2013.01); *A61K 2039/542* (2013.01); *A61K 2039/545* (2013.01); *A61K 2039/55555* (2013.01); *A61K 2039/55561* (2013.01); *C12N 2730/10134* (2013.01); *C12N 2770/32434* (2013.01)

(56) References Cited

U.S. PATENT DOCUMENTS

| | | |
|---|---|---|
| 4,349,538 A | 9/1982 | Levy |
| 4,352,884 A * | 10/1982 | Nakashima et al. .......... 435/180 |
| 4,436,727 A | 3/1984 | Ribi |
| 4,537,769 A | 8/1985 | Cerini |
| 4,866,034 A | 9/1989 | Ribi |
| 4,877,611 A | 10/1989 | Cantrell |
| 4,894,228 A | 1/1990 | Purcell et al. |
| 4,912,094 A | 3/1990 | Myers et al. |
| 4,983,387 A | 1/1991 | Goldstein et al. |
| 5,057,540 A | 10/1991 | Kensil et al. |
| 5,160,669 A | 11/1992 | Wallach et al. |
| 5,250,236 A | 10/1993 | Gasco |
| 5,340,588 A | 8/1994 | Domb |
| 5,393,527 A | 2/1995 | Malick et al. |
| 5,549,910 A | 8/1996 | Szoka, Jr. |
| 5,567,434 A | 10/1996 | Szoka, Jr. |
| 5,653,996 A | 8/1997 | Hsu |
| 5,679,355 A | 10/1997 | Alexander et al. |
| 5,817,318 A | 10/1998 | Sia et al. |
| 5,853,753 A | 12/1998 | Maierhofer et al. |
| 5,858,368 A | 1/1999 | Smith et al. |
| 5,861,243 A | 1/1999 | Dietrich et al. |
| 5,876,721 A | 3/1999 | Alexander et al. |
| 5,879,703 A | 3/1999 | Fountain |
| 5,910,306 A | 6/1999 | Alving et al. |
| 5,919,480 A | 7/1999 | Kedar et al. |
| 5,948,410 A | 9/1999 | Van Scharrenburg et al. |
| 5,962,298 A | 10/1999 | Fiers et al. |
| 5,977,081 A | 11/1999 | Marciani |
| 6,005,099 A | 12/1999 | Davies et al. |
| 6,080,725 A | 6/2000 | Marciani |
| 6,090,392 A | 7/2000 | Berman |
| 6,136,606 A | 10/2000 | Chatfield |
| 6,180,110 B1 | 1/2001 | Funkhouser et al. |
| 6,207,178 B1 * | 3/2001 | Westesen et al. .............. 424/405 |
| 6,235,888 B1 | 5/2001 | Pachuk et al. |
| 6,248,363 B1 | 6/2001 | Patel et al. |
| 6,287,570 B1 | 9/2001 | Foley |
| 6,290,967 B1 | 9/2001 | Volkin et al. |
| 6,303,347 B1 | 10/2001 | Johnson et al. |
| 6,344,354 B1 | 2/2002 | Webster et al. |
| 6,372,223 B1 | 4/2002 | Kistner et al. |
| 6,383,806 B1 | 5/2002 | Rios |
| 6,500,623 B1 | 12/2002 | Tung |
| 6,503,753 B1 | 1/2003 | Rios |
| 6,534,065 B1 | 3/2003 | Makin et al. |
| 6,538,123 B2 | 3/2003 | Barban |
| 6,541,003 B1 | 4/2003 | Smith |
| 6,605,457 B1 | 8/2003 | Fiers et al. |
| 6,635,246 B1 | 10/2003 | Barrett et al. |
| 6,649,410 B2 | 11/2003 | Rios |
| 6,653,130 B2 | 11/2003 | Rios |
| 6,692,955 B1 | 2/2004 | Meredith et al. |
| 6,706,859 B1 | 3/2004 | Sörensen |
| 6,740,325 B1 | 5/2004 | Arnon et al. |
| 6,743,900 B2 | 6/2004 | Burt et al. |
| 6,764,840 B2 | 7/2004 | Johnson et al. |
| 6,787,351 B2 | 9/2004 | Chen et al. |
| 6,831,169 B2 | 12/2004 | Pachuk et al. |
| 6,861,244 B2 | 3/2005 | Barrett et al. |
| 6,991,929 B1 | 1/2006 | D'hondt |
| 7,052,701 B2 | 5/2006 | Barrett et al. |
| 7,063,849 B1 | 6/2006 | Thibodeau et al. |
| 7,067,134 B1 | 6/2006 | Kang et al. |
| 7,192,595 B2 | 3/2007 | Arnon et al. |
| 7,244,435 B2 | 7/2007 | Lai |
| 7,262,045 B2 | 8/2007 | Schwartz et al. |
| 7,316,813 B2 | 1/2008 | Eichhorn |
| 7,348,011 B2 | 3/2008 | Guntaka et al. |
| 7,361,352 B2 | 4/2008 | Birkett et al. |
| 7,399,840 B2 | 7/2008 | Burt et al. |
| 7,468,259 B2 | 12/2008 | Fiers et al. |
| 7,494,659 B2 | 2/2009 | Katinger et al. |
| 7,510,719 B2 | 3/2009 | Dang et al. |
| 7,514,086 B2 | 4/2009 | Arnon et al. |
| 7,527,800 B2 | 5/2009 | Yang et al. |
| 7,537,768 B2 | 5/2009 | Luke et al. |
| 9,610,248 B2 * | 4/2017 | Anderson ............... A61K 9/127 |
| 2002/0164648 A1 | 11/2002 | Goins et al. |
| 2003/0092145 A1 | 5/2003 | Jira et al. |
| 2004/0011840 A1 | 2/2004 | Nagy et al. |
| 2004/0022840 A1 | 2/2004 | Nagy et al. |
| 2004/0081688 A1 * | 4/2004 | Del Curto et al. ............ 424/450 |
| 2005/0042230 A1 | 2/2005 | Anderson et al. |
| 2005/0095283 A1 | 5/2005 | Castor et al. |
| 2005/0169979 A1 | 8/2005 | Michaeli et al. |
| 2005/0214331 A1 * | 9/2005 | Levy .............................. 424/400 |
| 2006/0121105 A1 * | 6/2006 | Barenholz et al. ............ 424/450 |
| 2006/0257852 A1 | 11/2006 | Rappuoli et al. |
| 2007/0142315 A1 | 6/2007 | Forsbach et al. |
| 2007/0224257 A1 * | 9/2007 | Commander et al. ......... 424/450 |
| 2007/0264273 A1 | 11/2007 | Barenholz et al. |
| 2008/0057080 A1 | 3/2008 | Luke et al. |
| 2008/0131466 A1 * | 6/2008 | Reed et al. ................. 424/282.1 |
| 2008/0145375 A1 | 6/2008 | Bembridge et al. |
| 2008/0160089 A1 | 7/2008 | Vitiello et al. |
| 2008/0181914 A1 | 7/2008 | Eichhorn |
| 2008/0213461 A1 | 9/2008 | Gill et al. |
| 2008/0268028 A1 | 10/2008 | Zurbriggen et al. |
| 2008/0286353 A1 | 11/2008 | Gregoriadis |
| 2009/0028903 A1 | 1/2009 | Hanon et al. |
| 2009/0041809 A1 | 2/2009 | Emtage |
| 2009/0081157 A1 | 3/2009 | Kornbluth et al. |
| 2009/0081254 A1 | 3/2009 | Vajdy et al. |
| 2009/0117141 A1 | 5/2009 | Torres et al. |
| 2009/0155309 A1 | 6/2009 | Friede et al. |
| 2009/0181078 A1 | 7/2009 | Reed et al. |
| 2009/0202620 A1 | 8/2009 | Turnell et al. |
| 2010/0062071 A1 | 3/2010 | Loxley et al. |
| 2010/0080844 A1 | 4/2010 | Bacon et al. |
| 2010/0129392 A1 | 5/2010 | Shi et al. |
| 2010/0226932 A1 | 9/2010 | Smith et al. |
| 2011/0177163 A1 | 7/2011 | Diaz-Mitoma et al. |
| 2012/0177683 A1 | 7/2012 | Anderson et al. |
| 2012/0276125 A1 | 11/2012 | Ast et al. |
| 2013/0108692 A1 | 5/2013 | Anderson et al. |
| 2013/0295165 A1 | 11/2013 | Anderson et al. |
| 2013/0323280 A1 | 12/2013 | Anderson et al. |
| 2014/0356399 A1 | 12/2014 | Anderson |
| 2015/0079077 A1 | 3/2015 | Kirchmeier et al. |

FOREIGN PATENT DOCUMENTS

| | | |
|---|---|---|
| CA | 2803282 A1 | 1/2011 |
| CN | 1169161 A | 12/1997 |
| CN | 101574394 A | 11/2009 |
| EP | 0413637 A1 | 2/1991 |
| EP | 0 433242 A1 | 6/1991 |
| EP | 0489153 A1 | 6/1992 |
| EP | 729473 B1 | 8/2000 |

(56) References Cited

FOREIGN PATENT DOCUMENTS

| | | |
|---|---|---|
| EP | 1 129 723 A1 | 9/2001 |
| EP | 2 014 279 A1 | 1/2009 |
| GB | 2122204 | 1/1984 |
| WO | WO-88/06882 A1 | 9/1988 |
| WO | WO-90/02965 A1 | 3/1990 |
| WO | WO9029695 | 3/1990 |
| WO | WO-92/00081 A1 | 1/1992 |
| WO | WO-93/19781 A1 | 10/1993 |
| WO | WO-95/09651 A1 | 4/1995 |
| WO | WO-95/14026 A1 | 5/1995 |
| WO | WO-95/17210 A1 | 6/1995 |
| WO | WO9517210 | 6/1995 |
| WO | WO-96/11280 A1 | 4/1996 |
| WO | WO-97/04768 A1 | 2/1997 |
| WO | WO9801139 | 1/1998 |
| WO | WO-98/50399 A1 | 11/1998 |
| WO | WO-99/62500 A1 | 12/1999 |
| WO | WO-01/05374 A1 | 1/2001 |
| WO | WO-02/051390 A2 | 7/2002 |
| WO | WO-03/011223 A2 | 2/2003 |
| WO | WO-03/099195 A2 | 12/2003 |
| WO | WO-2005/117958 A1 | 12/2005 |
| WO | WO-2007/110776 A1 | 10/2007 |
| WO | WO-2008/153236 A1 | 12/2008 |
| WO | WO-2009/029695 A1 | 3/2009 |
| WO | WO-2009/091531 A2 | 7/2009 |
| WO | WO-2009/155489 A2 | 12/2009 |
| WO | WO-2010033812 A1 | 3/2010 |
| WO | WO-2011/005769 A1 | 1/2011 |
| WO | WO-2011/005772 A1 | 1/2011 |
| WO | WO-2012/006367 A2 | 1/2012 |
| WO | WO-2012/006368 A2 | 1/2012 |
| WO | WO-2012/097346 A1 | 7/2012 |
| WO | WO-2012/097347 A1 | 7/2012 |

OTHER PUBLICATIONS

MR Mozafari (editor). "Nanomaterials and Nanosystems for Biomedical Applications." Springer, ISBN 978-1-4020-6288-9 (HB) ISBN 978-1-4020-6289-6 (e-book), 2007, pp. 1-159, with additional unnumbered pages totaling 168 total sheets.*
JN Israelachvili, S Marcelja, RG Horn. "Physical Principles of Membrane Organization." Quarterly Reviews of Biophysics, vol. 13 No. 2, 1980, pp. 121-200.*
CAS Registry Record for Dimyristoyl phosphatidylcholine (CAS# 18656-38-7). Entered STN Nov. 16, 1984, 2 printed pages.*
E Bennett, AB Mullen, VA Ferro. "Translational Modifications to Improve Vaccine Efficacy in an Oral Influenza Vaccine." Methods, vol. 49, pp. 322-327, available online May 3, 2009. (Year: 2009).*
International Search Report for PCT/US10/41078 dated Aug. 23, 2010.
Written Opinion for PCT/US10/41078 dated Aug. 23, 2010.
Alexopoulou et al., "Preparation and characterization of lyophilized liposomes with incorporated quercetin," J Liposome Res. 16(1): 17-25, 2006.
Alpan et al., "The role of dentritic cells, B cells, and M cells in gut-oriented immune responses," J Immunol 166(8): 4843-4852, 2001.
Andre et al., "Inactivated candidate vaccines for hepatitis A," Prog Med Virol. 37: 72-95, 1990.
Bangham et al., "Diffusion of univalent ions across the lamellae of swollen phospholipids," J. Mol. Biol. 13(1): 238-252, 1965.
Cregg et al., "High-Level Expression and Efficient Assembly of Hepatitis B Surface Antigen in the Methylotrophic Yeast, Pichia Pastoris," Biotechnology 5: 479-485, 1987.
Fattovich G., "Natural history of hepatitis B," J Hepatol. 39 Suppl 1: S50-S58, 2003.
Field et al., "Inducers of interferon and host resistance. II. Multistranded synthetic polynucleotide complexes," Proc Natl Acad Sci USA 58(3): 1004-1010, 1967.
Harford et al., "Expression of hepatitis B surface antigen in yeast," Dev Biol Stand. 54: 125-130, 1983.
Hilleman MR., "Critical overview and outlook: pathogenesis, prevention, and treatment of hepatitis and hepatocarcinoma caused by hepatitis B virus," Vaccine 21(32): 4626-4649, 2003.
International Search Report for PCT/US10/41081, dated Oct. 26, 2010.
Kasrian and DeLuca, "Thermal Analysis of the Tertiary Butyl Alcohol-Water System and Its Implications on Freeze-Drying," Pharm. Res., 12(4): 484-490, 1995.
Kasrian and DeLuca, "The Effect of Tertiary Butyl Alcohol on the Resistance of the Dry Product Layer During Primary Drying," Pharm. Res., 12(4): 491-495, 1995.
Levy et al., "Inhibition of tumor growth by polyinosinic-polycytidylic acid," Proc Natl Acad Sci USA 62(2): 357-361, 1969.
Li and Deng, "A novel method for the preparation of liposomes: freeze drying of monophase solutions," J Pharm Sci 93(6): 1403-1414, 2004.
Mao et al., "Further evaluation of the safety and protective efficacy of live attenuated hepatitis A vaccine (H2-strain) in humans," Vaccine 15(9): 944-947, 1997.
McAleer et al., "Human hepatitis B vaccine from recombinant yeast," Nature 307(5947): 178-180, 1984.
Miller et al., "Hepatitis C virus shares amino acid sequence similarity with pestiviruses and flaviviruses as well as members of two plant virus supergroups," Proc. Natl. Acad. Sci. 87: 2057-2061, 1990.
Mowat AM, "Dentritic cells and immune responses to orally administered antigens," Vaccine 23(15): 1797-1799, 2005.
Provost et al., "New findings in live, attenuated hepatitis A vaccine development," J Med Virol. 20(2): 165-175, 1986.
Valenzuela et al., "Chemical synthesis of a gene for human epidermal growth factor urogastrone and its expression in yeast," Proc Natl. Acad Sci USA 80(24): 7461-7465, 1983.
Walde and Ichikawa, "Enzymes inside lipid vesicles: preparation, reactivity and applications," Biomol Eng. 18(4): 143-177, 2001.
Weiner et al., "Variable and hypervariable domains are found in the regions of HCV corresponding to the flavivirus envelope and NS1 proteins and the pestivirus envelope glycoproteins," Virology 180(2): 842-848, 1991.
Written Opinion for PCT/US10/41081, dated Oct. 26, 2010.
Yan et al., "Recent Advances in Liposome-Based Nanoparticles for Antigen Delivery," Polymer Reviews 47(3): 329-344, 2007.
International Preliminary Report on Patentability for PCT/US2010/041078, dated Jan. 19, 2012 (12 pages).
International Preliminary Report on Patentability for PCT/US2010/041081, dated Jan. 19, 2012 (9 pages).
Lasic, D.D., Novel Applications of Lipsomes, TIBTECH, 16:307-321 (1998).
Mann et al., Optimisation of a Lipid Based Oral Delivery System Containing A/Panama Influenza Haemagglutinin, Vaccine, 22:2425-2429 (2004).
Collins et al., Non-Ionic Surfactant Vesicle Formulation of Stibogluconate for Canine Leishmaniasis, Journal of Pharmacy and Pharmacology, 42(S1):53P (1990).
Kirby et al., Dehydration-Rehydration Vesicles: A Simple Method for High Yield Drug Entrapment in Liposomes, Nature Biotechnology, 2(11):979-984 (1984).
Pick, Liposomes with a Large Trapping Capacity Prepared by Freezing and Thawing of Sonicated Phospholipid Mixtures, Arch. Biochem. Biophys, 212(1):186-194 (1981).
Varun, T. et al., Niosomes and Liposomes—Vesicular Approach Towards Transdermal Drug Delivery, International Journal of Pharmaceutical and Chemical Sciences, 1(3):632-644 (2012).
Chen et al., Research advances on Solid lipid nanoparticles as new drug carrier, Chinese Journal of Ethnomedicine and Ethnopharmacy, Issue 2, pp. 7-10, (2009).
Chen et al., An overview of liposome lyophilization and its future potential, Journal of Controlled Release, 142: 299-311 (2010).
Hassan, Y. et al., Immune responses in mice induced by HSV-1 glycoproteins presented with ISCOMs or NISV delivery systems, Vaccine, 14(17-18):1581-9 (1996).

(56) References Cited

OTHER PUBLICATIONS

Huckriede, A. et al., The virosome concept for influenza vaccines, Vaccine, 23 Suppl 1:S26-38 (2005).
Jurk, et al., Modulating Responsiveness of Human TLR7 and 8 to Small Molecule Ligands with T-rich Phosphorothiate Oligodeoxynucleotides, Eur J Immunol., 36(7):1815-26 (2006).
Khmelnitsky et al., Denaturation capacity: a new quantitative criterion for selection of organic solvents as reaction media in biocatalysis, European Journal of Biochem., 198:31-41, (1991).
Lavanchy, The Importance of Global Surveillance of Influenza, Vaccine, 17:S24-S25 (1999).
Russell, DG and Alexander, J., Effective immunization against cutaneous leishmaniasis with defined membrane antigens reconstituted into liposomes, Journal of Immunology, 40(4):1274-1279 (1988).
Salager, J.-L., Surfactants—Types and Uses, FIRP Booklet #E300-A, Teaching Aid in Surfactant Science & Engineering, in English, Laboratory of Formulation, Interfaces, Rheology and Processes, Universidad de Los Andes, Version 2: 1-50 (2002).
Schalk, JA et al., Estimation of the number of infectious measles viruses in live virus vaccines using quantitative real-time PCR, Journal of Virological Methods, 117(2):179-187 (2004).
Schubert et al., Solvent Injection as a New Approach for Manufacturing Lipid Nanoparticles—Evaluation of the Method and Process Parameters, European Journal of Pharmaceuticals and Biopharmaceutics, 55:125-131 (2003).
Uchegbu, I.F. and Vyas, S.P., Non-ionic surfactant based vesicles (niosomes) in drug delivery, in International Journal of Pharmaceuticals, 172:33-70 (1998).
Vangala et al., A comparative study of cationic liposome and niosome-based adjuvant systems for protein subunit vaccines: characterisation, environmental scanning electron microscopy and immunisation studies in mice, Journal of Pharmacy and Pharmacology, 58:787-799, (2006).
Verma, S. et al., Nanoparticle vesicular systems: A versatile tool for drug delivery, Journal of Chemical and Pharmaceutical Research, 2(2):496-509 (2010).
Wagner et al., Liposome Technology for Industrial Purposes, J. Drug Delivery, vol. 2011, Article ID 591325 (9 pages) (2010).
Wang et al., Solvent Injection-Lyophilization of Tert-Butyl Alcohol/Water Cosolvent Systems for the Preparation of Drug-Loaded Solid Lipid Nanoparticles, Colloids and Surfaces B: Biointerfaces, 79:254-261 (2010).

World Health Organization, The Immunological Basis for Immunization Series, Model 7: Measles (2009).
Holland, H.E.J. et al., Nonionic Surfactant Vesicles: A Study Vesicle Formation, Characterization and Stability, Journal of Colloid and Interface Science, 161(2): 366-376, Abstract Only, 2 pages (1993).
Kumar, G.P. et al., Nonionic surfactant vesicular systems for effective drug delivery—an overview, Acta Pharmaceutica Sinica B, 1(4): 208-219 (2011).
Mann et al., Optimisation of a Lipid Based Oral Delivery System Containing A/Panama Influenza Haemagglutinin, Vaccine, 22: 2425-2429 (2004).
Oku, et al., Effect of serum protein binding on real-time trafficking of liposomes with different charges analyzed by positron emission tomography, Biochimica et Biophysica Acta, 1280:149-154 (1996).
Tarekegn, A. et al., Niosomes in Targeted Drug Delivery: Some Recent Advances, International Journal of Pharmaceutical Sciences and Research, 1(9): 1-8 (2010).
Anderson, R.J., Properties of Cholesterol Obtained from Different Sources, J. Biol. Chem., 71: 4007-418 (1927).
Bramwell, V. et al., Particulate delivery systems for vaccines: what can we expect?, The Journal of Pharmacy and Pharmacology, 58(6): 717-728 (2006).
Conacher, M. et al., Oral immunisation with peptide and protein antigens by formulation in lipid vesicles incorporating bile salts (bilosomes), Vaccine, 19(20-22): 2965-2974 (2001).
Gnjatic, S. et al., TLR Agonists, The Cancer Journal, 16(4): 382-391 (2010).
Jiang et al., Advances in non-ionic surfactant based vesicles, Chinese Journal of Modern Drug Application, 1:(11): 98-101 (2007). English Translation, pp. 1-8.
Manosroi, A. et al., Characterization of vesicles prepared with various non-ionic surfactants mixed with cholesterol, Colloids and Surfaces B: Biointerfaces, 30(1-2): 129-138 (2003).
Senior, J. and Radomsky, M., Liposomes for Local Sustained Drug Release, Sustained-Release Injectable Products, Chapter 7: 137-180 (Published Sep. 30, 2005).
Van Hal, D. A. et al., Preparation and Characterization of Nonionic Surfactant Vesicles, Journal of Colloid and Interface Science, 178(1): 263-273 (1996).
Bennett, E. et al., Translational modifications to improve vaccine efficacy in an oral influenza vaccine, methods, 49: 322-327 (2009).

* cited by examiner

METHODS FOR PREPARING VESICLES AND FORMULATIONS PRODUCED THEREFROM

CROSS REFERENCE TO RELATED APPLICATIONS

The present application is the National Stage of International Application No. PCT/US2010/041078, filed Jul. 6, 2010, which claims priority under 35 U.S.C. §119(e) to U.S. provisional application Ser. No. 61/223,196, filed Jul. 6, 2009 and U.S. provisional application Ser. No. 61/256,912, filed Oct. 30, 2009, the entire contents of each of which are hereby incorporated by reference.

BACKGROUND

Vesicles were first described in the 1960s as a model of cellular membranes (see Bangham et al., *J. Mol. Biol.* 13:238-252, 1965). Vesicles have found a number of applications in the delivery of small molecule drugs, vaccine adjuvancy, gene transfer and diagnostic imaging (e.g., see *Liposome Technology*, $3^{rd}$ Edition, Edited by Gregory Gregoriadis, Informa HealthCare, 2006 and *Liposomes: A Practical Approach* (*The Practical Approach Series*, 264), $2^{nd}$ Edition, Edited by Vladimir Torchilin and Volkmar Weissig, Oxford University Press, USA, 2003).

A number of methods for preparing vesicles have been described (e.g., see references cited above and Walde and Ichikawa, *Biomol. Eng.*, 18:143-177, 2001). However, there remains a need in the art for methods that can be used to entrap substances within vesicles.

One method that has been described in the art is the so-called 3-step melt method. Vesicle-forming lipids are initially melted at high temperatures (e.g., 120° C.). An emulsion is created in a second step by adding an aqueous buffer (e.g., bicarbonate buffer) to the molten lipids. Finally, the substance to be entrapped is homogenized with the components of the emulsion at a reduced temperature (e.g., 50° C.) prior to lyophilization. Alternatively, vesicles from the emulsion are lyophilized and then reconstituted in the presence of the substance to be entrapped.

While methods such as this one may well be suitable for entrapping substances that can withstand high temperatures and/or small molecules that are able to diffuse rapidly into empty vesicles we have found that they are unsuitable for entrapping the types of antigens (e.g., polypeptides, viruses, etc.) that are commonly involved in vaccines. In particular, we have found that these methods produce low entrapment efficiencies and can dramatically reduce the activity of the underlying antigen (e.g., as measured by immune responses). There is therefore a need in the art for methods of preparing vesicles that are capable of entrapping antigens while minimizing impact on antigen activity.

SUMMARY

In one aspect, the present disclosure provides methods for preparing vesicles which include steps of providing a molten mixture of vesicle-forming lipids and then adding the molten mixture to an aqueous solution comprising an antigen such that antigen-containing vesicles are formed.

In another aspect, the present disclosure provides methods for preparing vesicles which include steps of providing a lyophilized lipid product and rehydrating the lyophilized lipid product with an aqueous solution comprising an antigen such that antigen-containing vesicles are formed. The lyophilized lipid product is prepared by melting vesicle-forming lipids to produce a molten lipid mixture and then lyophilizing the molten lipid mixture.

In another aspect, the present disclosure provides antigen-containing vesicle formulations prepared using these methods. In some embodiments, the antigen-containing vesicle formulations exhibit antigen entrapment levels that are higher than those obtainable using prior art methods. In some embodiments, the antigen-containing vesicle formulations exhibit antigen activity levels that are higher than those obtainable using prior art methods.

In yet another aspect, the present disclosure provides kits that include a lyophilized lipid product in a first container and an aqueous solution comprising an antigen in a second container. In some embodiments, the kit also includes instructions for mixing the contents of the two containers in order to produce antigen-containing vesicle formulations.

DEFINITIONS

Figure 1:
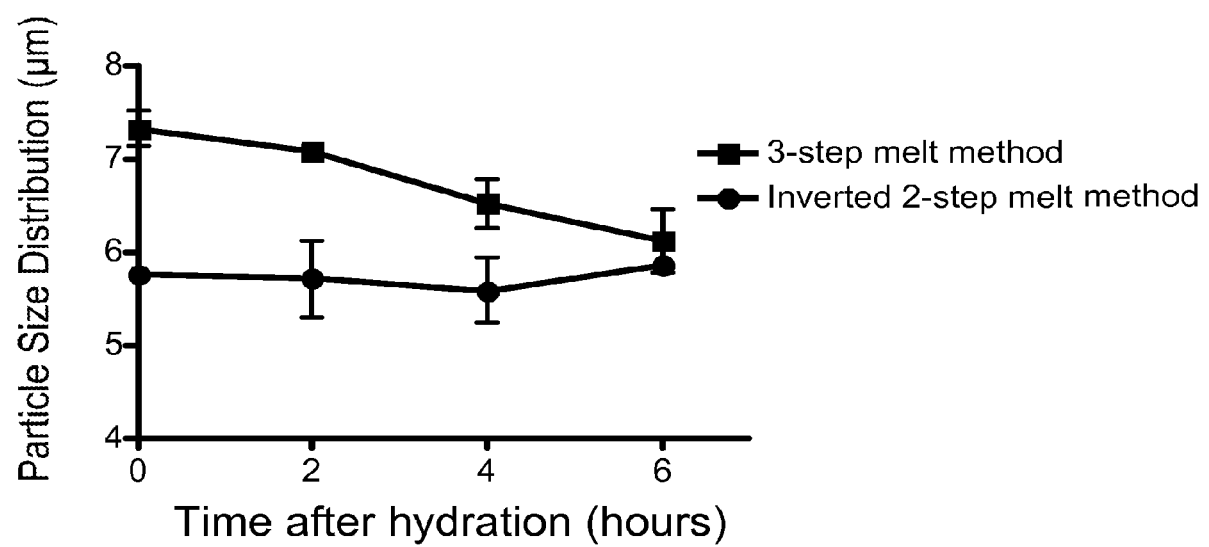
FIG. 1 compares the mean particle sizes for two vesicle formulations that were prepared using the 3-step melt method of Example 1 and the inverted 2-step melt method of Example 2. Formulations were lyophilized and then rehydrated in the presence of buffer containing 2 µg of inactivated hepatitis A antigen. Vesicle size, which is a good marker of stability, was measured using a mastersizer immediately after hydration and 2, 4, and 6 hours afterwards.

Throughout the present disclosure, several terms are employed that are defined in the following paragraphs.

As used herein, the term "antigen" refers to a substance containing one or more epitopes (either linear, conformational or both) that can be recognized by an antibody. In certain embodiments, an antigen can be a virus, a polypeptide, a polynucleotide, a polysaccharide, etc. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. In certain embodiments, an antigen may be an "immunogen."

As used herein, the term "entrapping" refers to any kind of physical association between a substance and a vesicle, e.g., encapsulation, adhesion (to the inner or outer wall of the vesicle) or embedding in the wall with or without extrusion of the substance. The term is used interchangeably with the terms "loading" and "containing".

As used herein, the terms "immune response" refer to a response elicited in an animal. An immune response may refer to cellular immunity, humoral immunity or may involve both. An immune response may also be limited to a part of the immune system. For example, in certain embodiments, an immunogenic formulation may induce an increased IFNγ response. In certain embodiments, an immunogenic formulation may induce a mucosal IgA response (e.g., as measured in nasal and/or rectal washes). In certain embodiments, an immunogenic formulation may induce a systemic IgG response (e.g., as measured in scrum).

As used herein, the term "immunogenic" means capable of producing an immune response in a host animal against a non-host entity (e.g., a hepatitis A virus or a hepatitis B virus). In certain embodiments, this immune response forms the basis of the protective immunity elicited by a vaccine against a specific infectious organism (e.g., a hepatitis A virus or a hepatitis B virus). An "immunogen" is an immunogenic substance (e.g., a molecule).

As used herein, the terms "therapeutically effective amount" refer to the amount sufficient to show a meaningful benefit in a patient being treated. The therapeutically effective amount of an immunogenic formulation may vary depending on such factors as the desired biological endpoint, the nature of the formulation, the route of administration, the health, size and/or age of the patient being treated, etc.

As used herein, the term "polypeptide" refers to a protein (i.e., a string of at least two amino acids linked to one another by peptide bonds). In some embodiments, polypeptides may include moieties other than amino acids (e.g., may be glycoproteins, proteoglycans, lipoproteins, etc.) and/or may be otherwise processed or modified. Those of ordinary skill in the art will appreciate that a "protein" can be a complete polypeptide chain as produced by a cell (with or without a signal sequence), or can be a portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, etc. In some embodiments, polypeptides may comprise natural amino acids, non-natural amino acids, synthetic amino acids, and combinations thereof.

As used herein, the term "polysaccharide" refers to a polymer of sugars. The polymer may include natural sugars (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified sugars (e.g., 2'-fluororibose, 2'-deoxyribose, and hexose). Exemplary polysaccharides include starch, glycogen, dextran, cellulose, etc.

As used herein, the term "polynucleotide" refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

As used herein, the term "small molecule therapeutic" refers to a non-polymeric therapeutic molecule that may contain several carbon-carbon bonds and have a molecular weight of less than about 1500 Da (e.g., less than about 1000 Da, less than about 500 Da or less than about 200 Da). A small molecule therapeutic can be synthesized in a laboratory (e.g., by combinatorial synthesis, using an engineered microorganism, etc.) or can be found in nature (e.g., a natural product). In general, a small molecule therapeutic may alter, inhibit, activate, or otherwise affect a biological event. For example, small molecule therapeutics may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. A more complete listing of exemplary small molecules suitable for use in the methods of the present disclosure may be found in *Pharmaceutical Substances: Syntheses, Patents, Applications*, Edited by Axel Kleemann and Jurgen Engel, Thieme Medical Publishing, 1999; *Merck Index: An Encyclopedia of Chemicals, Drugs, and Biologicals*, Edited by Susan Budavari et al., CRC Press, 1996, and the *United States Pharmacopeia-25/National formulary-20*, published by the United States Pharmacopeial Convention, Inc., 2001. Preferably, though not necessarily, the small molecule is one that has already been deemed safe and effective for use by the appropriate governmental agency or body. For example, drugs for human use listed by the FDA under 21 C.F.R. §§330.5, 331 through 361, and 440 through 460 and drugs for veterinary use listed by the FDA under 21 C.F.R. §§500 through 589, are all considered acceptable for use in accordance with the methods of the present disclosure.

As used herein, the term "treat" (or "treating", "treated", "treatment", etc.) refers to the administration of a formulation to a patient who has a disease, a symptom of a disease or a predisposition toward a disease, with the purpose to alleviate, relieve, alter, ameliorate, improve or affect the disease, a symptom or symptoms of the disease, or the predisposition toward the disease. In certain embodiments, the term "treating" refers to the vaccination of a patient.

DETAILED DESCRIPTION OF SOME EMBODIMENTS

I. Methods for Preparing Vesicles

The present disclosure provides methods for preparing vesicles. Vesicles generally have an aqueous compartment enclosed by one or more bilayers which include lipids, optionally with other molecules. For example, as discussed in more detail below, in some embodiments, the vesicles of the present disclosure comprise transport enhancing molecules (e.g., bile salts) which facilitate the transport of lipids across mucosal membranes.

In one aspect, the present disclosure provides methods for preparing vesicles which include steps of providing a molten mixture of vesicle-forming lipids and then adding the molten mixture to an aqueous solution comprising an antigen such that antigen-containing vesicles are formed. In some embodiments, the aqueous solution comprising an antigen is temperature controlled. In some embodiments, the aqueous solution comprising an antigen is kept at a temperature of less than about 50° C. during the step of adding (e.g., less than about 40° C., less than about 30° C., etc.). In some embodiments, the aqueous solution comprising an antigen is kept at a temperature range between about 25° C. and about 50° C. In some embodiments, the aqueous solution comprising an antigen is kept at room temperature.

It is to be understood that a molten mixture of vesicle-forming lipids may be obtained in any manner, e.g., lipids are melted to form a molten mixture. In some embodiments, lipids are melted at a temperature range between 120° C. and 150° C. (e.g., between 120° C. and 125° C., between 120° C. and 130° C., between 120° C. and 140° C., between 130° C. and 140° C., between 135° C. and 145° C., or between 140° C. and 145° C.). In some embodiments, lipids are melted at about 120° C. In some embodiments, lipids are melted at about 125° C. In some embodiments, lipids are melted at about 130° C. In some embodiments, lipids are melted at about 135° C. In some embodiments, lipids are melted at about 140° C. In some embodiments, lipids are melted at about 145° C. In some embodiments, lipids are melted at about 150° C.

In another aspect, the present disclosure provides methods for preparing vesicles which include steps of providing a lyophilized lipid product and rehydrating the lyophilized lipid product with an aqueous solution comprising an antigen such that antigen-containing vesicles are formed. The lyophilized lipid product is prepared by melting vesicle-forming lipids to produce a molten lipid mixture and then lyophilizing the molten lipid mixture.

Without wishing to be bound to any theory, it is thought that by adding an aqueous solution of antigens to the lyophilized lipid product, vesicles are formed in the presence of the antigen. This may explain the high entrapment efficiencies observed. Additionally, the methods of the present disclosure avoid exposing antigen to organic solvents and high temperatures. Without wishing to be limited to any theory, this may explain the high activity (i.e., antigenicity and/or immunogenicity) of the entrapped antigens in the resulting formulations.

Vesicle-Forming Lipids

Lipids are organic molecules that are generally insoluble in water but soluble in nonpolar organic solvents (e.g., ether, chloroform, acetone, benzene, etc.). Fatty acids are one class of lipids that include an acid moiety linked to a saturated or unsaturated hydrocarbon chain. Specific examples include lauric acid, palmitic acid, stearic acid, arachidic acid, palmitoleic acid, oleic acid, linoleic acid, linolenic acid, arachidonic acid, etc. Alkali metal salts of fatty acids are typically more soluble in water than the acids themselves. Fatty acids and their salts that include hydrocarbon chains with eight or more carbons often exhibit amphiphilic properties due to the presence of both hydrophilic (head) and hydrophobic (tail) regions in the same molecule. Non-ionic lipids that include polar head groups can also exhibit amphiphilic (i.e., surfactant) properties. The triesters of fatty acids with glycerol (1,2,3-trihydroxypropane) compose another class of lipids known as triglycerides that are commonly found in animal fats and plant oils. Esters of fatty acids with long chain monohydric alcohols form another class of lipids that are found in waxes. Phospholipids are yet another class of lipids. They resemble the triglycerides in being ester or amide derivatives of glycerol or sphingosine with fatty acids and phosphoric acid. The phosphate moiety of the resulting phosphatidic acid may be further esterified with ethanolamine, choline or serine in the phospholipid itself. It is to be understood that the methods may be used with any lipid that is capable of forming vesicles including any of the lipids that are described in the prior art (e.g., in *Liposome Technology*, $3^{rd}$ Edition, Edited by Gregory Gregoriadis, Informa HealthCare, 2006 and *Liposomes: A Practical Approach* (*The Practical Approach Series*, 264), $2^{nd}$ Edition, Edited by Vladimir Torchilin and Volkmar Weissig, Oxford University Press, USA, 2003).

In some embodiments, the vesicle-forming lipid is a phospholipid. Any naturally occurring or synthetic phospholipid can be used. Without limitation, examples of specific phospholipids are L-α-(distearoyl) lecithin, L-α-(diapalmitoyl) lecithin, L-α-phosphatide acid, L-α-(dilauroyl)-phosphatidic acid, L-α(dimyristoyl)phosphatidic acid, L-α(dioleoyl)phosphatidic acid, DL-α(dipalmitoyl)phosphatidic acid, L-α(distearoyl)phosphatidic acid, and the various types of L-α-phosphatidylcholines prepared from brain, liver, egg yolk, heart, soybean and the like, or synthetically, and salts thereof.

In some embodiments, the vesicle-forming lipid is a non-ionic surfactant. Non-ionic surfactant vesicles are referred to herein as "NISVs". Without limitation, examples of suitable non-ionic surfactants include ester-linked surfactants based on glycerol. Such glycerol esters may comprise one of two higher aliphatic acyl groups, e.g., containing at least ten carbon atoms in each acyl moiety. Surfactants based on such glycerol esters may comprise more than one glycerol unit, e.g., up to 5 glycerol units. Glycerol monoesters may be used, e.g., those containing a $C_{12}$-$C_{20}$alkanoyl or alkenoyl moiety, for example caproyl, lauroyl, myristoyl, palmitoyl, oleyl or stearoyl. An exemplary non-ionic surfactant is 1-monopalmitoyl glycerol.

In some embodiments, ether-linked surfactants may also be used as the non-ionic surfactant. For example, ether-linked surfactants based on glycerol or a glycol having a lower aliphatic glycol of up to 4 carbon atoms, such as ethylene glycol, are suitable. Surfactants based on such glycols may comprise more than one glycol unit, e.g., up to 5 glycol units (e.g., diglycolcetyl ether and/or polyoxyethylene-3-lauryl ether). Glycol or glycerol monoethers may be used, including those containing a $C_{12}$-$C_{20}$ alkanyl or alkenyl moiety, for example capryl, lauryl, myristyl, cetyl, oleyl or stearyl. Ethylene oxide condensation products that can be used include those disclosed in PCT Publication No. WO88/06882 (e.g., polyoxyethylene higher aliphatic ether and amine surfactants). Exemplary ether-linked surfactants include 1-monocetyl glycerol ether and diglycolcetyl ether.

Other Components

In some embodiments, the vesicles may contain other lipid and non-lipid components, as long as these do not prevent vesicle formation. It is to be understood that these components may be co-mixed with the vesicle-forming lipids and/or may be co-mixed with the antigen(s). In some embodiments, we have found that it can be advantageous to co-mix these components with the vesicle-forming lipids.

In some embodiments, the vesicles may include a transport enhancing molecule which facilitates the transport of lipids across mucosal membranes. As described in U.S. Pat. No. 5,876,721, a variety of molecules may be used as transport enhancers. For example, cholesterol derivatives in which the $C_{23}$ carbon atom of the side chain carries a carboxylic acid, and/or derivatives thereof, may be used as transport enhancers. Such derivatives include, but are not limited to, the "bile acids" cholic acid and chenodeoxycholic acid, their conjugation products with glycine or taurine such as glycocholic and taurocholic acid, derivatives including deoxycholic and ursodeoxycholic acid, and salts of each of these acids. NISVs that further include a bile acid or salt are referred to herein as "bilosomes". In some embodiments, transport enhancers include acyloxylated amino acids, such as acylcarnitines and salts thereof. For example, acylcarnitine containing $C_{6-20}$ alkanoyl or alkenoyl moieties, such as palmitoylcarnitine, may be used as transport enhancers. As used herein, the term acyloxylated amino acid is intended to cover primary, secondary and tertiary amino acids as well as α, β, and γ amino acids. Acylcarnitines are examples of acyloxylated γ amino acids. It is to be understood that vesicles may comprise more than one type of transport enhancer, e.g., one or more different bile salts and one or more acylcarnitines. The transport enhancer(s), if present, will typically comprise between 40 and 400% percent by weight of the vesicle-forming lipid (e.g., between 60 and 100% by weight or between 70 and 90% by weight). In some embodiments, the transport enhancer(s), if present will comprise between 1 and 40% percent by weight of the vesicle-forming lipid (e.g., between 1 and 20% by weight, between 1 and 25% by weight, between 1 and 30% by weight, between 1 and 35% by weight, between 2 and 25% by weight, between 2 and 30% by weight or between 2 and 35% by weight).

In certain embodiments, the vesicles may lack a transport enhancing molecule. In some embodiments, the vesicles may lack a "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, the vesicles may lack acyloxylated amino acids, such as acylcarnitines and salts thereof, and palmitoylcarnitines.

In some embodiments, the vesicles may include an ionic surfactant, e.g., to cause the vesicles to take on a negative charge. For example, this may help to stabilize the vesicles and provide effective dispersion. Without limitation, acidic materials such as higher alkanoic and alkenoic acids (e.g., palmitic acid, oleic acid) or other compounds containing acidic groups including phosphates such as dialkyl phosphates (e.g., dicetylphospate, or phosphatidic acid or phosphatidyl serine) and sulphate monoesters such as higher alkyl sulphates (e.g., cetylsulphate), may all be used for this purpose. The ionic surfactant(s), if present, will typically comprise, between 1 and 30% by weight of the vesicle-forming lipid. For example, between 2 and 20% by weight or between 5 and 15% by weight. In some embodiments, the ionic surfactant(s), if present, will comprise between 1 and 50% by weight of the vesicle-forming lipid (e.g., between 1 and 35% by weight, between 5 and 40% by weight, between 10 and 40% by weight, between 15 and 40% by weight, between 20 and 40% by weight, or between 20 and 35% by weight).

In some embodiments, the vesicles may include an appropriate hydrophobic material of higher molecular mass that facilitates the formation of bilayers (such as a steroid, e.g., a sterol such as cholesterol). In some embodiments, the presence of the steroid may assist in forming the bilayer on which the physical properties of the vesicle depend. The steroid, if present, will typically comprise between 20 and 120% by weight of the vesicle-forming lipid. For example, between 25 and 90% by weight or between 35 and 75% by weight. In some embodiments, the steroid, if present, will comprise between 25 and 95% by weight, between 25 and 105% by weight, between 35 and 95% by weight, or between 35 and 105% by weight of the vesicle-forming lipid.

In some embodiments, a lyoprotectant may be included in any solution or mixture prior to lyophilization. Exemplary lyoprotectants include sucrose, trehalose, polyethylene glycol (PEG), dimethyl-succinate buffer (DMS), bovine serum albumin (BSA), mannitol and dextran.

In some embodiments, vesicles of the present disclosure are bilosomes that further include an ionic surfactant or a steroid. In some embodiments, the bilosomes may include both an ionic surfactant and a steroid.

In some embodiments, vesicles of the present disclosure are non-ionic surfactant vesicles (NISVs) that lack a transport enhancing molecule and that further include an ionic surfactant or a steroid. In some embodiments, the vesicles may lack a "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, the vesicles may lack acyloxylated amino acids, such as acylcarnitines and salts thereof, and palmitoylcarnitines. In some embodiments, the NISVs may lack a transport enhancing molecule (e.g., any of the aforementioned molecules) and include both an ionic surfactant and a steroid.

Lyophilization

As discussed above and below, in some embodiments, the methods of the present disclosure include a lyophilizing step (whether of a molten lipid mixture or of a formulation of antigen-containing vesicles). Lyophilization is an established method used to enhance the long-term stability of products. Enhancement of physical and chemical stability is thought to be accomplished by preventing degradation and hydrolysis. Lyophilization involves freezing the preparation in question and then reducing the surrounding pressure (and optionally heating the preparation) to allow the frozen solvent(s) to sublime directly from the solid phase to gas (i.e., drying phase). In certain embodiments, the drying phase is divided into primary and secondary drying phases.

The freezing phase can be done by placing the preparation in a container (e.g., a flask, eppendorf tube, etc.) and optionally rotating the container in a bath which is cooled by mechanical refrigeration (e.g., using dry ice and methanol, liquid nitrogen, etc.). In some embodiments, the freezing step involves cooling the preparation to a temperature that is below the eutectic point of the preparation. Since the eutectic point occurs at the lowest temperature where the solid and liquid phase of the preparation can coexist, maintaining the material at a temperature below this point ensures that sublimation rather than evaporation will occur in subsequent steps.

The drying phase (or the primary drying phase when two drying phases are used) involves reducing the pressure and optionally heating the preparation to a point where the solvent(s) can sublimate. This drying phase typically removes the majority of the solvent(s) from the preparation. It will be appreciated that the freezing and drying phases are not necessarily distinct phases but can be combined in any manner. For example, in certain embodiments, the freezing and drying phases may overlap.

A secondary drying phase can optionally be used to remove residual solvent(s) that was adsorbed during the freezing phase. Without wishing to be bound to any theory, this phase involves raising the temperature to break any physico-chemical interactions that have formed between the solvent molecules and the frozen preparation. Once the drying phase is complete, the vacuum can be broken with an inert gas (e.g., nitrogen or helium) before the lyophilized product is optionally sealed.

Rehydration

As discussed above, in some embodiments, the methods of the present disclosure include a step of rehydrating a lyophilized lipid product to form antigen-containing vesicles. This is achieved by mixing the lyophilized lipid product with an aqueous solution comprising an antigen. In some embodiments, this involves adding the aqueous solution to the lyophilized lipid product.

In some embodiments, the antigen-containing vesicles contain at least about 10% of the antigen added in the step of rehydrating. In some embodiments, the antigen-containing vesicles contain at least about 20% of the antigen added in the step of rehydrating. In some embodiments, the antigen-containing vesicles contain at least about 30% of the antigen added in the step of rehydrating. In some embodiments, the antigen-containing vesicles contain at least about 40% of the antigen added in the step of rehydrating. In some embodiments, the antigen-containing vesicles contain at least about 50% of the antigen added in the step of rehydrating. In some embodiments, the antigen-containing vesicles contain at least about 60% of the antigen added in the step of rehydrating. In some embodiments, the antigen-containing vesicles contain at least about 70% of the antigen added in the step of rehydrating. In some embodiments, the antigen-containing vesicles contain at least about 80% of the antigen added in the step of rehydrating. In some embodiments, the antigen-containing vesicles contain at least about 90% of the antigen added in the step of rehydrating.

In some embodiments, the aqueous solution includes a buffer. The buffer used will typically depend on the nature of the antigen or antigens in the aqueous solution. For example, without limitation, a PCB buffer, an $Na_2HPO_4/NaH_2PO_4$ buffer, a PBS buffer, a bicine buffer, a Tris buffer, a HEPES buffer, a MOPS buffer, etc. may be used. PCB buffer is produced by mixing sodium propionate, sodium cacodylate, and bis-Tris propane in the molar ratios 2:1:2. Varying the amount of HCl added enables buffering over a pH range from 4-9. In some embodiments, a carbonate buffer may be used.

In some embodiments, a formulation of antigen-containing vesicles prepared by any of the aforementioned methods may be lyophilized for future use and subsequently rehydrated (e.g., with sterile water or an aqueous buffer) prior to use. In some embodiments, an adjuvant may be added during this rehydration step (e.g., by inclusion in the sterile water or aqueous buffer). In some embodiments, a formulation of antigen-containing vesicles may be stored at −80° C. prior to lyophilization. In some embodiments, a lyophilized formulation may be stored at a range of temperatures between −20° C. and 10° C. (e.g., between −5° C. and 10° C., between 0° C. and 5° C. or between 2° C. and 8° C.).

Vesicle Size and Processing

It will be appreciated that a vesicle formulation will typically include a mixture of vesicles with a range of sizes. It is to be understood that the diameter values listed below correspond to the most frequent diameter within the mixture. In some embodiments >90% of the vesicles in a formulation will have a diameter which lies within 50% of the most frequent value (e.g., 1000±500 nm). In some embodiments the distribution may be narrower, e.g., >90% of the vesicles in a formulation may have a diameter which lies within 40, 30, 20, 10 or 5% of the most frequent value. In some embodiments, sonication or ultra-sonication may be used to facilitate vesicle formation and/or to alter vesicle particle size. In some embodiments, filtration, dialysis and/or centrifugation may be used to adjust the vesicle size distribution.

In general, vesicles produced in accordance with the methods of the present disclosure may be of any size. In some embodiments, the formulations may include vesicles with a diameter in the range of about 150 nm to about 15 µm, e.g., about 800 nm to about 1.5 µm. In certain embodiments, the vesicles may have a diameter which is greater than 10 µm, e.g., about 15 µm to about 25 µm. In certain embodiments, the vesicles may have a diameter in the range of about 2 µm to about 10 µm, e.g., about 1 µm to about 4 µm. In certain embodiments, the vesicles may have a diameter which is less than 150 nm, e.g., about 50 nm to about 100 nm.

Antigens

In general it is to be understood that any antigen or antigens may be entrapped using a method of the present disclosure. As previously discussed, the antigen or antigens may be associated with vesicles in any manner. In some embodiments, the antigen or antigens may be present in the aqueous core of the vesicles. However, depending on its hydrophobicity, an antigen may also be partially or completely associated with a bilayer. In general it is also to be understood that in some embodiments, a vesicle formulation may include amounts of one or more antigens that are not associated with vesicles.

In some embodiments, the methods of the present disclosure may be used to entrap one or more of the antigens included in a vaccine. Table 1 is a non-limiting list of suitable vaccines.

TABLE 1

| Vaccine | Disease |
|---|---|
| BioThrax ® | Anthrax |
| DTaP (Daptacel ®, Infanrix ®, Tripedia ®) | Diphtheria |
| Td (Decavac ®) | Diphtheria |
| DT, TT | Diphtheria |
| Tdap (Boostrix ®, Adaccl ®) | Diphtheria |
| DTaP/IPV/HepB (Pediarix ®) | Diphtheria |
| DTaP/Hib (TriHIBit ®) | Diphtheria |
| HepA (Havrix ®, Vaqta ®) | Hepatitis A |
| HepA/HepB (Twinrix ®) | Hepatitis A |
| HepB (Engerix-B ®, Recombivax HB ®) | Hepatitis B |
| HepB/Hib (Comvax) | Hepatitis B |
| DTaP/IPV/HepB (Pediarix), | Hepatitis B |
| HepA/HepB (Twinrix ®) | Hepatitis B |
| Hib (ActHIB ®, HibTITER ®, PedvaxHIB ®) | HIB |

TABLE 1-continued

| Vaccine | Disease |
| --- | --- |
| HepB/Hib (Comvax ®) | HIB |
| DTaP/Hib (TriHIBit ®) | HIB |
| HPV (Gardasil ®) | HPV |
| Influenza (Fluarix ®, Fluvirin ®, Fluzone ®, Flulaval ®, FluMist ®) | Seasonal influenza |
| Influenza (Afluria ®) | Seasonal influenza |
| Influenza (Agriflu ®) | Seasonal influenza |
| Influenza (Begrivac ®) | Seasonal influenza |
| Influenza (Enzira ®) | Seasonal influenza |
| Influenza (Fluad ®) | Seasonal influenza |
| Influenza (Fluvax ®) | Seasonal influenza |
| Influenza (Fluviral, Fluviral S/F ®) | Seasonal influenza |
| Influenza (Grippol ®) | Seasonal influenza |
| Influenza (Inflexal, Inflexal S, Inflexal V ®) | Seasonal influenza |
| Influenza (Influvac ®) | Seasonal influenza |
| Influenza (Mastaflu ®) | Seasonal influenza |
| Influenza (Mutagrip ®) | Seasonal influenza |
| Influenza (Optaflu ®) | Seasonal influenza |
| Influenza (Vaxigrip ®) | Seasonal influenza |
| H1N1 pandemic influenza (Arepanrix ®) | H1N1 pandemic influenza |
| H1N1 pandemic influenza (Calvapan ®) | H1N1 pandemic influenza |
| H1N1 pandemic influenza (Focetria ®) | H1N1 pandemic influenza |
| H1N1 pandemic influenza (Influenza A (H1N1) 2009 Monovalent Vaccine ®) | H1N1 pandemic influenza |
| H1N1 pandemic influenza (Pandemrix ®) | H1N1 pandemic influenza |
| JE (JE-Vax ®) | Japanese Encephalitis |
| Lyme Disease (LYMErix ®) | Lyme Disease |
| Measles (Attenuvax ®) | Measles |
| MMR (M-M-R II ®) | Measles |
| MMRV (ProQuad ®) | Measles |
| Mening. Conjugate (Menactra ®) | Meningococcal |
| Mening. Polysaccharide (Menomune ®) | Meningococcal |
| Mumps (Mumpsvax ®) | Mumps |
| MMR (M-M-R II ®) | Mumps |
| MMRV (ProQuad ®) | Mumps |
| DTaP (Daptacel ®, Infanrix ®, Tripedia ®) | Pertussis |
| Tdap (Boostrix ®) | Pertussis |
| DTaP/IPV/HepB (Pediarix ®) | Pertussis |
| DTaP/Hib (TriHIBit ®) | Pertussis |
| Pneumo. Conjugate (Prevnar ®) | Pneumococcal |
| Pneumo. Polysaccharide (Pneumovax 23 ®) | Pneumococcal |
| Polio (Ipol ®) | Polio |
| DTaP/IPV/HepB (Pediarix ®) | Polio |
| Rabies (BioRab ®, Imovax Rabies ®, RabAvert ®) | Rabies |
| Rotavirus (RotaTeq ®) | Rotavirus |
| Rubella (Meruvax II ®) | Rubella |
| MMR (M-M-R II ®) | Rubella |
| MMRV (ProQuad ®) | Rubella |
| Shingles (Zostavax ®) | Shingles |
| Vaccinia (Dryvax ®) | Smallpox and Monkeypox |
| DTaP (Daptacel ®, Infanrix ®, Tripedia ®) | Tetanus |
| Td (Decavac ®) | Tetanus |
| DT, TT | Tetanus |
| Tdap (Boostrix ®) | Tetanus |
| DTaP/IPV/HepB (Pediarix ®) | Tetanus |
| DTaP/Hib (TriHIBit ®) | Tetanus |
| BCG | Tuberculosis |
| Typhoid (Typhim Vi ®) | Typhoid |
| Typhoid oral (Vivotif Berna ®) | Typhoid |
| Varicella (Varivax ®) | Chickenpox (Varicella) |
| MMRV (ProQuad ®) | Chickenpox (Varicella) |
| Yellow Fever (YF-Vax ®) | Yellow Fever |

In the following sections we discuss some exemplary antigens that could be used.

Hepatitis A

Hepatitis A is a serious liver disease caused by the hepatitis A virus (HAV). The virus is found in the stools of persons with hepatitis A. As shown in Table 1, several inactivated hepatitis A vaccines are currently licensed. For example, Havrix® is manufactured by GlaxoSmithKline Biologicals. U.S. Pat. No. 6,180,110 describes the attenuated HAV strain (HAV 4380) used in Havrix® which was originally derived from the HM175 strain of HAV (U.S. Pat. No. 4,894,228). Havrix® contains a sterile suspension of formalin inactivated HAV. The viral antigen activity is referenced to a standard using an ELISA and expressed in terms of ELISA Units (U). Each 1 ml adult dose of vaccine consists of 1440 U of viral antigen, adsorbed on 0.5 mg of aluminum as aluminum hydroxide (alum). Havrix® (as with all other licensed hepatitis A vaccines) is supplied as a sterile suspension for intramuscular (IM) administration. Although one dose of Havrix® provides at least short-term protection, a second booster dose after six to twelve months is currently recommended to ensure long-term protection.

Another example of an inactivated hepatitis A vaccine, AIMMUGEN® has been licensed and marketed in Japan since 1994 by Kaketsuken. AIMMUGEN® contains a sterile suspension of formaldehyde inactivated HAV. The recommended adult dose is 0.5 µg IM at 0, 1 and 6 months.

As used herein the expression "HAV antigen" refers to any antigen capable of stimulating neutralizing antibody to HAV in humans. The HAV antigen may comprise live attenuated virus particles or inactivated attenuated virus particles or may be, for example an HAV capsid or HAV viral protein, which may conveniently be obtained by recombinant DNA technology.

In one aspect, the present disclosure provides methods for preparing immunogenic formulations that include an inactivated or attenuated hepatitis A virus (also called "hepatitis A viral antigen" or "viral antigen" herein). It will be appreciated that the methods may be used to prepare an inactivated hepatitis A virus. In general, these methods will involve propagating a hepatitis A virus in a host cell, lyzing the host cell to release the virus, isolating and then inactivating the viral antigen. After removal of the cell culture medium, the cells are lysed to form a suspension. This suspension is purified through ultrafiltration and gel permeation chromatography procedures. The purified lysate is then treated with formalin to ensure viral inactivation (e.g., see Andre et al., *Prog. Med. Virol.* 37:72-95, 1990).

In preparing AIMMUGEN®, hepatitis A virus strain KRM0003 (established from a wild-type HAV, which had been isolated from the feces of a hepatitis A patient) is propagated in GL37 cells (a cell strain established for vaccine production from a parent cell strain of African green monkey kidney). The GL37 cells are inoculated with HAV strain KRM0003 and viral antigen is harvested, extensively purified and inactivated with formaldehyde.

Another example of an inactivated hepatitis A virus that is commercially available but is not a licensed vaccine is hepatitis A antigen (HAV-ag) from Meridian Life Sciences. Like Havrix® the Meridian HAV-ag also derives from hepatitis A virus strain HM175 but it is propagated in FRhK-4 (fetal rhesus kidney) cells. After removal of cell culture medium, the cells are lysed to form a suspension and the suspension is partially purified by gradient centrifugation and inactivated by treatment with formalin.

It will be appreciated that any hepatitis A virus strain may be used, e.g., without limitation any of the following strains which have been described in the art (and other non-human variants):

Human hepatitis A virus Hu/Arizona/HAS-15/1979
Human hepatitis A virus Hu/Australia/HM175/1976
Human hepatitis A virus Hu/China/H2/1982
Human hepatitis A virus Hu/Costa Rica/CR326/1960

Human hepatitis A virus Hu/France/CF-53/1979
Human hepatitis A virus Hu/Georgia/GA76/1976
Human hepatitis A virus Hu/Germany/GBM/1976
Human hepatitis A virus Hu/Japan/HAJ85-1/1985
Human hepatitis A virus Hu/Los Angelos/LA/1975
Human hepatitis A virus Hu/Northern Africa/MBB/1978
Human hepatitis A virus Hu/Norway/NOR-21/1998
Human hepatitis A virus Hu/Sierra Leone/SLF88/1988
Human hepatitis A virus MSM1
Human hepatitis A virus Shanghai/LCDC-1/1984

In addition, while formalin and formaldehyde are commonly used to inactivate licensed hepatitis A vaccines it is to be understood that other techniques could be used, e.g., treatment with chlorine, exposure to high temperatures (the viral antigen is inactivated above 85° C./185° F.), etc.

In certain embodiments it may prove advantageous to add additional steps to the traditional method for preparing an inactivated hepatitis A virus. For example, U.S. Pat. No. 6,991,929 describes including a protease treatment step (e.g., trypsin) after the virus has been propagated. This step was found to improve the removal of host cell material and yield a purer viral preparation.

While all currently licensed hepatitis A vaccines include inactivated viral antigens, alternative vaccines which include attenuated viral antigen have also been described in the literature. In certain embodiments, an immunogenic formulation may comprise such an attenuated viral antigen. As is well known in the art, the advantage of an attenuated vaccine lies in the potential for higher immunogenicity which results from its ability to replicate in vivo without causing a full infection.

One method which has been used in the art to prepare attenuated hepatitis A viruses is viral adaptation which involves serially passing a viral strain through multiple cell cultures. Over time the strain mutates and attenuated strains can then be identified. In certain embodiments the virus may be passed through different cell cultures. For example, researchers have generated attenuated hepatitis A viruses by passing strain CR326 sixteen times in human diploid lung (MRCS) cell cultures (see Provost et al., *J. Med. Virol.* 20:165-175, 2005). A slightly more virulent strain was obtained by passing the same strain fifteen times in fetal rhesus monkey kidney (FRhK6) cell cultures plus eight times in MRCS cell cultures. An alternative attenuated hepatitis A vaccine which was prepared in this fashion from the H2 strain has also been described (see European Patent No. 0413637 and Mao et al., *Vaccine* 15:944-947, 1997).

In certain embodiments it may prove advantageous to perform one or more of the cell culture steps at a reduced temperature. For example, European Patent No. 0413637 describes including one or more inoculation steps in which the temperature is reduced (e.g., to 32-34° C. instead of 35-36° C.).

U.S. Pat. No. 6,180,110 describes an attenuated hepatitis A virus (HAV 4380) which grows in MRC-5 cells. The researchers identified mutations in HAV 4380 which appeared to be associated with attenuation by comparing its genome with the genome of a more virulent strain. This allowed them to design mutant HAV strains with optimal characteristics for a candidate attenuated hepatitis A vaccine. It will be appreciated that this approach could be applied to any known attenuated hepatitis A virus and used to genetically engineer variants without the need for viral adaptation.

Hepatitis B

Hepatitis B virus (HBV) causes both acute and chronic infections. The wide clinical spectrum of HBV infection ranges from sub clinical to acute symptomatic hepatitis; from an inactive hepatitis B surface antigen (HBsAg) carrier state to liver cirrhosis and its complications during chronic phase (Fattovich, *J. Hepatol.* 39:s50-58, 2003). HBV is transmitted on parenteral or mucosal exposure to HBsAg positive body fluids generally from HBV infected persons (Hilleman, *Vaccine* 21:4626-4649, 2003).

Currently, there are two commercial vaccines used to prevent HBV infection, both are manufactured using recombinant technology. For example, Engerix-B™ is a noninfectious recombinant DNA hepatitis B vaccine developed by GlaxoSmithKline Biologicals. It contains purified surface antigen of HBV obtained by culturing genetically engineered *Saccharomyces cervisiae* cells, which carry the surface antigen gene of HBV.

As used herein the expression "Hepatitis B surface antigen" or "HBsAG" refers to any HBsAG antigen or fragment thereof displaying the antigenicity of HBV surface antigen in humans.

Engerix-B™ and other licensed hepatitis B vaccines, which are administered parentally, have been successful in inducing a systemic immune response to HBV. However, the antibodies produced as part of the systemic immune response are unable to provide protection at the level of mucosa, which is the major entry site for most infectious agents including HBV. There therefore remains a need in the art for an orally delivered hepatitis B vaccine.

In one aspect, the present disclosure provides methods for preparing immunogenic formulations that include a hepatitis B virus surface antigen or a fragment thereof displaying the antigenicity of HBsAG. All known hepatitis B vaccines include a recombinant HBsAG. It is to be understood that any one of these licensed hepatitis B vaccines may be used as a source of antigen in a method of the present disclosure to produce an immunogenic formulation.

In general, any method may be used to prepare hepatitis B surface antigen. The preparation of HBsAg is well documented (e.g., see Harford et al., *Develop. Biol. Standard* 54: 125, 1983 and Gregg et al., *Biotechnology* 5:479, 1987 among others). In general, recombinant DNA technology methods may be used which involve culturing genetically engineered cells, which carry the surface antigen gene of HBV. The surface antigen expressed is then purified and normally formulated as a suspension of the surface antigen adsorbed on aluminum hydroxide (e.g., see Valenzuela et al., *Proc. Natl. Acad. Sci. USA* 80:1-5, 1983 and McAleer et al., *Nature* 307:178-180, 1984).

Influenza

Influenza is a common infectious disease of the respiratory system associated with the Orthomyxoviridae family of viruses. Influenza A and B are the two types of influenza viruses that cause epidemic human disease. Influenza A viruses are further categorized into subtypes on the basis of two surface antigens: hemagglutinin (HA) and neuraminidase (N). Influenza B viruses are not categorized into subtypes. Vaccination is recognized as the single most effective way of preventing or attenuating influenza for those at high risk of serious illness from influenza infection and related complications. The inoculation of antigen prepared from inactivated influenza virus stimulates the production of specific antibodies. Protection is generally afforded only against those strains of virus from which the vaccine is prepared or closely related strains.

Influenza vaccines, of all kinds, are usually trivalent vaccines. They generally contain antigens derived from two influenza A virus strains and one influenza B strain. The influenza virus strains to be incorporated into influenza vaccines each season are determined by the World Health Organization (WHO) in collaboration with national health authorities and vaccine manufacturers. It will be appreciated that any influenza virus strain may be used in accordance with the present disclosure, and that influenza virus strains will differ from year to year based on WHO recommendations.

Monovalent vaccines, which may be useful for example in a pandemic situation, are also encompassed. A monovalent, pandemic flu vaccine will most likely contain influenza antigen from a single A strain. In some embodiments, influenza antigens are derived from pandemic influenza strains. For example, in some embodiments, influenza antigens are influenza A (H1N1 of swine origin) viral antigens.

Predominantly three types of inactivated vaccines are used worldwide to protect against influenza: whole virus vaccines, split virus vaccines containing external and internal components of the virus, and subunit vaccines composed of just external components of the virus (hemagglutinin and neuraminidase). Without wishing to be limited to any theory, it is thought that the higher purity of subunit vaccines should make them less reactogenic and better tolerated. Conversely whole virus and split virus vaccines are thought to contain more epitopes and so be more immunogenic.

In some embodiments, influenza antigens are based on subunit vaccines. Generally, subunit vaccines contain only those parts of the influenza virus that are needed for effective vaccination (e.g., eliciting a protective immune response). In some embodiments, subunit influenza antigens are prepared from virus particles (e.g., purification of particular components of the virus). In some embodiments, subunit influenza antigens are prepared by recombinant methods (e.g., expression in cell culture). For example, U.S. Pat. No. 5,858,368 describes methods of preparing a recombinant influenza vaccine using recombinant DNA technology. The resulting trivalent influenza vaccine is based on a mixture of recombinant hemagglutinin antigens cloned from influenza viruses having epidemic potential. The recombinant hemagglutinin antigens are full length, uncleaved, glycoproteins produced from baculovirus expression vectors in cultured insect cells and purified under non-denaturing conditions. In some embodiments, subunit influenza antigens are generated by synthetic methods (e.g., peptide synthesis). Subunit vaccines may contain purified surface antigens, hemagglutinin antigens and neuraminidase antigens prepared from selected strains determined by the WHO. Without wishing to be bound by any theories, it is thought that surface antigens, hemagglutinin antigens and neuramidase antigens play a significant role in eliciting production of virus neutralizing antibodies upon vaccination.

In some embodiments, influenza antigens are split virus antigens. Vaccines prepared using split virus antigens typically contain a higher concentration of the most immunogenic portions of the virus (e.g., hemagglutinin and neuramidase), while lowering the concentration of less immunogenic viral proteins as well as non-viral proteins present from eggs (used to produce virus) or extraneous agents (e.g., avian leukosis virus, other microorganisms and cellular debris). Generally, split virus antigens are prepared by a physical process that involves disrupting the virus particle, generally with an organic solvent or a detergent (e.g., Triton X-100), and separating or purifying the viral proteins to varying extents, such as by centrifugation over a sucrose gradient or passage of allantoic fluid over a chromatographic column. In some embodiments, disruption and separation of virus particles is followed by dialysis or ultrafiltration. Split virus antigens usually contain most or all of the virus structural proteins although not necessarily in the same proportions as they occur in the whole virus. Methods of viral splitting as well as suitable splitting agents are known in the art (see for example U.S. Patent Publication No. 20090155309). In some embodiments, final antigen concentration (e.g., of hemagglutinin and/or neuramidase antigens) of split viral antigen is standardized using methods known in the art (e.g., ELISA).

In some embodiments, influenza antigens are whole virus antigens. It is thought that in unprimed individuals, vaccines prepared with whole virus antigens may be more immunogenic and induce higher protective antibody response at a lower antigen dose that other formulations (e.g., subunit or split virus antigens). However, influenza vaccines that include whole virus antigens can produce more side effects than other formulations.

Influenza viral antigens present in immunogenic formulations described herein may be infectious, inactivated or attenuated.

In certain embodiments, an immunogenic formulation may comprise an inactivated viral antigen. It will be appreciated that any method may be used to prepare an inactivated influenza viral antigen. WO 09/029,695 describes exemplary methods for producing a whole inactivated virus vaccine. In general, these methods will involve propagating an influenza virus in a host cell, optionally lysing the host cell to release the virus, isolating and then inactivating the viral antigen. Chemical treatment of virus (e.g., formalin, formaldehyde, among others) is commonly used to inactivate virus for vaccine formulation. However, it is to be understood that other techniques could be used, e.g., treatment with chlorine, exposure to high temperatures, etc. In these treatments the outer virion coat is typically left intact while the replicative function is impaired. Non-replicating virus vaccines preferably contain more antigen than live vaccines that are able to replicate in the host.

In certain embodiments, an immunogenic formulation may comprise an attenuated viral antigen. As is well known in the art, one advantage of a vaccine prepared with an attenuated viral antigen lies in the potential for higher immunogenicity which results from its ability to replicate in vivo without causing a full infection. Live virus vaccines that are prepared from attenuated strains preferably lack pathogenicity but are still able to replicate in the host. One method which has been used in the art to prepare attenuated influenza viral antigens is viral adaptation which involves serially passing a viral strain through multiple cell cultures. Over time the strain mutates and attenuated strains can then be identified. In certain embodiments the virus may be passed through different cell cultures. In certain embodiments it may prove advantageous to perform one or more of the cell culture steps at a reduced temperature.

Several influenza vaccines are currently licensed (see Table 1). For example, Fluzone®, which is a split cell inactivated influenza vaccine, is developed and manufactured by Sanofi Pasteur, Inc. and may be used in accordance with the present disclosure. Fluzone® contains a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a nonionic surfactant, octoxinol-9, (Triton® X-100) producing a split viral antigen. The split virus is then further purified by chemical means and suspended in sodium phosphate-buffered isotonic sodium chloride solution. Fluzone® vaccine is then standardized according to requirements for the influenza season and is formulated to contain 45 μg hemagglutinin (HA) per 0.5 mL dose, in the recommended ratio of 15 μg HA each, representative of the three prototype strains (e.g., 2007-2008 vaccine prepared with A/Solomon Islands/3/2006 (H1N1), A/Wisconsin/67/2005 (H3N2) and B/Malaysia/2506/2004 strains). Fluzone® vaccine is formulated for intramuscular injection.

Another example of a licensed influenza vaccine that may be used in accordance with the present disclosure is Vaxigrip®, which is a split cell inactivated influenza vaccine also developed and manufactured by Sanofi Pasteur, Inc. Vaxigrip® is prepared in a similar fashion to the process outlined above for Fluzone® and is similarly formulated for intramuscular injection.

Yet another example of a licensed influenza vaccine that may be used in accordance with the present disclosure is Flumist®. Flumist® is a live, attenuated trivalent vaccine for administration by intranasal spray. The influenza virus strains in Flumist® have three genetic mutations that lead to temperature restricted growth and an attenuated phenotype. The cumulative effect of the antigenic properties and the genetically modified influenza viruses is that they are able to replicate in the nasopharynx and induce protective immunity. In order to produce Flumist®, specific pathogen-free (SPF) eggs are inoculated with each of the appropriate viral strains and incubated to allow vaccine virus replication. The allantoic fluid of these eggs is harvested, pooled and then clarified by filtration. The virus is concentrated by ultracentrifugation and diluted with stabilizing buffer to obtain the final sucrose and potassium phosphate concentrations. Viral harvests are then sterile filtered to produce the monovalent bulks. Monovalent bulks from the three strains are subsequently blended and diluted as required to attain the desired potency with stabilizing buffers to produce the trivalent bulk vaccine. The bulk vaccine is then filled directly into individual sprayers for nasal administration. Each pre-filled refrigerated Flumist® sprayer contains a single 0.2 mL dose. Each 0.2 mL dose contains $10^{6.5-7.5}$ FFU of live attenuated influenza virus reassortants of each of the appropriate three viral strains.

As described above, several influenza vaccines are currently licensed. It is to be understood that any one or combination of these licensed influenza vaccines may be combined with a vesicle as described herein to produce an immunogenic formulation. For example, commercial Fluzone® and/or Vaxigrip® may be combined in this manner to produce an active immunogenic formulation. In some embodiments, licensed influenza vaccines are first purified (e.g., to remove alum adjuvant or other reagents in the vaccine). In some embodiments, licensed influenza vaccines are not purified prior to formulation with a vesicle as described herein.

PCT Patent Application No. PCT/US09/47911 describes some other exemplary influenza antigens that could be used in the methods and formulations of the present disclosure. Exemplary influenza antigens have also been described in U.S. Pat. Nos. 7,527,800; 7,537,768; 7,514,086; 7,510,719; 7,494,659; 7,468,259; 7,399,840; 7,361,352; 7,316,813; 7,262,045; 7,244,435; 7,192,595; 7,052,701; 6,861,244; 6,743,900; 6,740,325; 6,635,246; 6,605,457; 6,534,065; 6,372,223; 6,344,354; 6,287,570; 6,136,606; 5,962,298; 5,948,410; and 5,919,480.

Other Viruses

Hepatitis C virus (HCV) is now recognized as being the primary cause of transfusion-associated non-A, non-B (NANB) hepatitis. HCV is a single stranded, positive sense RNA virus with similarities to flaviviruses and pestiviruses (Miller et al., *Proc. Natl. Acad. Sci.* 87: 2057, 1991 and Weiner et al., *Virology* 180: 842, 1990). U.S. Pat. Nos. 7,348,011; 6,831,169; 6,538,123 and 6,235,888 all describe exemplary HCV antigens that could be employed in a vaccine.

The human immunodeficiency retrovirus (HIV) is responsible for AIDS (acquired immunodeficiency syndrome), a disease in which the body's immune system breaks down leaving it vulnerable to opportunistic infections. U.S. Pat. Nos. 7,067,134; 7,063,849; 6,787,351; 6,706,859; 6,692,955; 6,653,130; 6,649,410; 6,541,003; 6,503,753; 6,500,623; 6,383,806; 6,090,392; 5,861,243; 5,817,318; and 4,983,387 all describe exemplary HIV antigens that could be employed in a vaccine. Various HIV antigens are also disclosed in U.S. Patent Application Publication Nos. 20090117141 and 20090081254.

In certain embodiments, an immunogenic formulation that is prepared in accordance with the methods of the present disclosure may comprise an antigen that is thermolabile. As used herein, the terms "thermolabile antigen" refer to an antigen that loses antigenic integrity when exposed to certain elevated temperatures. In some embodiments, exposure of a thermolabile antigen to elevated temperatures destroys over 20% of the antigenic integrity of the antigen (e.g., over 30%, over 40%, over 50% or more) as measured in an antigenic integrity assay (e.g., an ELISA) as compared to the un-manipulated antigen. In certain embodiments, a thermolabile antigen loses antigenic integrity at temperatures above 30° C. (e.g., above 35° C., above 40° C., above 45° C., or above 50° C.). In some embodiments, storage of a thermolabile antigen at one of these elevated temperatures for more than 3 minutes (e.g., 5 minutes, 10 minutes, 15 minutes or more) destroys over 20% of the antigenic integrity of the antigen (e.g., over 30%, over 40%, over 50% or more) as measured in an antigenic integrity assay (e.g., an ELISA) as compared to the un-manipulated antigen. As discussed above, methods of the present disclosure are particularly beneficial for thermolabile antigens because they can utilize a lower temperature of antigen solution, allowing for better preservation of antigenic integrity.

It is to be understood that the present disclosure is not limited to antigens and that, in general, the methods may be used to entrap any substance whether antigenic or non-antigenic. Therefore, in some embodiments, the methods of the present disclosure may be used to entrap one or more polypeptides, polynucleotides or polysaccharides that may or may not be antigenic. Specific classes of substances include, but are not limited to, adjuvants, enzymes, receptors, neurotransmitters, hormones, cytokines, cell response modifiers such as growth factors and chemotactic factors, antibodies, haptens, toxins, interferons, ribozymes, antisense agents, plasmids, DNA, and RNA. In some embodiments the polypeptide may be an antibody or antibody fragment, e.g., a humanized antibody. In some embodiments, these substances are thermolabile in that they convert into degradants under the conditions referenced above in the context of antigens.

Adjuvants

In certain embodiments, the methods of the present disclosure may further include a step of adding one or more adjuvants to a vesicle formulation. As is well known in the art, adjuvants are agents that enhance immune responses. Adjuvants are well known in the art (e.g., see "Vaccine Design: The Subunit and Adjuvant Approach", *Pharmaceutical Biotechnology*, Volume 6, Eds. Powell and Newman, Plenum Press, New York and London, 1995). In some embodiments, an adjuvant may be added once the vesicle formulation (with entrapped antigen) has been prepared. In some embodiments, an adjuvant may be added during the process of preparing the vesicle formulations (e.g., along with vesicle-forming lipids or other vesicle components, along with the antigen or in a dedicated step).

In certain embodiments, an adjuvant is added before antigen is added. In some embodiments, adjuvant is co-melted with vesicle-forming lipids. In some embodiments, a TLR-4 adjuvant (described below) is co-melted with vesicle-forming lipids. In certain embodiments, an adjuvant is added after an antigen is added. In some embodiments, adjuvant is added along with a lyoprotectant after an antigen is added. In some embodiments, a TLR-3 adjuvant (described below) is added along with a lyoprotectant after an antigen is added. In some embodiments, the lyoprotectant is sucrose.

Exemplary adjuvants include complete Freund's adjuvant (CFA), incomplete Freund's adjuvant (IFA), squalene, squalane and alum (aluminum hydroxide), which are materials well known in the art, and are available commercially from several sources. In certain embodiments, aluminum or calcium salts (e.g., hydroxide or phosphate salts) may be used as adjuvants. Alum (aluminum hydroxide) has been used in many existing vaccines. Typically, about 40 to about 700 μg of aluminum is included per dose when given IM. For example, Havrix® includes 500 μg of aluminum per dose.

In various embodiments, oil-in-water emulsions or water-in-oil emulsions can also be used as adjuvants. For example, the oil phase may include squalene or squalane and a surfactant. In various embodiments, non-ionic surfactants such as the mono- and di-$C_{12}$-$C_{24}$-fatty acid esters of sorbitan and mannide may be used. The oil phase preferably comprises about 0.2 to about 15% by weight of the immunogenic formulation (e.g., about 0.2 to 1%). PCT Publication No. WO 95/17210 describes exemplary emulsions.

The adjuvant designated QS21 is an immunologically active saponin fractions having adjuvant activity derived from the bark of the South American tree Quillaja Saponaria Molina, and the methods of its production is disclosed in U.S. Pat. No. 5,057,540. Semi-synthetic and synthetic derivatives of Quillaja Saponaria Molina saponins are also useful, such as those described in U.S. Pat. Nos. 5,977,081 and 6,080,725.

TLRs are a family of proteins homologous to the Drosophila Toll receptor, which recognize molecular patterns associated with pathogens and thus aid the body in distinguishing between self and non-self molecules. Substances common in viral pathogens are recognized by TLRs as pathogen-associated molecular patterns. For example, TLR-3 recognizes patterns in double-stranded RNA, TLR-4 recognizes patterns in lipopolysaccharides while TLR-7/8 recognize patterns containing adenosine in viral and bacterial RNA and DNA. When a TLR is triggered by such pattern recognition, a series of signaling events occurs that leads to inflammation and activation of innate and adaptive immune responses. A number of synthetic ligands containing the molecular patterns recognized by various TLRs are being developed as adjuvants and may be included in an immunogenic formulation as described herein.

For example, polyriboinosinic:polyribocytidylic acid or poly(I:C) (available from InvivoGen of San Diego, Calif.) is a synthetic analog of double-stranded RNA (a molecular pattern associated with viral infection) and an exemplary adjuvant that is an agonist for TLR-3 (e.g., see Field et al., Proc. Natl. Acad. Sci. USA 58:1004 (1967) and Levy et al., Proc. Natl. Acad. Sci. USA 62:357 (1969)). In some embodiments, poly(I:C) may be combined with other agents to improve stability (e.g., by reducing degradation via the activity of RNAses). For example, U.S. Pat. Nos. 3,952,097; 4,024,241 and 4,349,538 describe poly(I:C) complexes with poly-L-lysine. The addition of poly-arginine to poly(I:C) has also been shown to reduce degradation via the activity of RNAses. Poly(IC:LC) is a synthetic, double-stranded poly (I:C) stabilized with poly-L-lysine carboxymethyl cellulose. U.S. Patent Publication No. 20090041809 describes double-stranded nucleic acids with one or more than one locked nucleic acid (LNA) nucleosides that can act as TLR-3 agonists. Those skilled in the art will be able to identify other suitable TLR-3 agonist adjuvants.

Attenuated lipid A derivatives (ALD) such as monophosphoryl lipid A (MPL) and 3-deacyl monophosphoryl lipid A (3D-MPL) are exemplary adjuvants that are agonists for TLR-4. ALDs are lipid A-like molecules that have been altered or constructed so that the molecule displays lesser or different of the adverse effects of lipid A. These adverse effects include pyrogenicity, local Shwarzman reactivity and toxicity as evaluated in the chick embryo 50% lethal dose assay ($CELD_{50}$). MPL and 3D-MPL are described in U.S. Pat. Nos. 4,436,727 and 4,912,094, respectively. MPL was originally derived from lipid A, a component of enterobacterial lipopolysaccharides (LPS), a potent but highly toxic immune system modulator. 3D-MPL differs from MPL in that the acyl residue that is ester linked to the reducing-end glucosamine at position 3 has been selectively removed. It will be appreciated that MPL and 3D-MPL may include a mixture of a number of fatty acid substitution patterns, i.e., heptaacyl, hexaacyl, pentaacyl, etc., with varying fatty acid chain lengths. Thus, various forms of MPL and 3D-MPL, including mixtures thereof, are encompassed by the present disclosure.

In some embodiments these ALDs may be combined with trehalosedimycolate (TDM) and cell wall skeleton (CWS), e.g., in a 2% squalene/Tween™ 80 emulsion (e.g., see GB Patent No. 2122204). MPL is available from Avanti Polar Lipids, Inc. of Alabaster, Ala. as PHAD (phosphorylated hexaacyl disaccharide). Those skilled in the art will be able to identify other suitable TLR-4 agonist adjuvants. For example, other lipopolysaccharides have been described in PCT Publication No. WO 98/01139; U.S. Pat. No. 6,005,099 and EP Patent No. 729473.

II. Vesicle Formulations

In another aspect, the present disclosure provides antigen-containing vesicle formulations prepared using these methods. In some embodiments, the antigen-containing vesicle formulations exhibit antigen entrapment levels that are higher than those obtainable using prior art methods. In some embodiments, the antigen-containing vesicle formulations exhibit antigen activity (i.e., antigenicity and/or immunogenicity) levels that are higher than those obtainable using prior art methods.

Immunogenic vesicle formulations are useful for treating many diseases in humans including adults and children. In general however they may be used with any animal. In certain embodiments, the methods herein may be used for veterinary applications, e.g., canine and feline applications. If desired, the methods herein may also be used with farm animals, such as ovine, avian, bovine, porcine and equine breeds.

Immunogenic vesicle formulations described herein will generally be administered in such amounts and for such a time as is necessary or sufficient to induce an immune response. Dosing regimens may consist of a single dose or a plurality of doses over a period of time. The exact amount of antigen to be administered may vary from patient to patient and may depend on several factors. Thus, it will be appreciated that, in general, the precise dose used will be as determined by the prescribing physician and will depend not only on the weight of the patient and the route of administration, but also on the frequency of dosing, the age of the patient and the severity of the symptoms and/or the risk of infection. In certain embodiments, the dose of antigen in an immunogenic formulation may range from about 5 µg to about 5 mg, e.g., from about 100 µg to about 750 µg. Lower doses of antigen may be sufficient when using sublingual or buccal administration, or in the presence of adjuvant. Higher doses may be more useful when given orally, especially in the absence of adjuvants.

In general, the formulations may be administered to a patient by any route. In particular, the results in the Examples demonstrate that the immunogenic formulations described herein can induce a protective response even when administered orally. It will be appreciated that the oral route is particularly desirable in light of the advantages of oral delivery over any form of injection (i.e., compliance, mass distribution, etc.). It will also be appreciated that the results are unexpected in light of the fact that most vaccines (including all known hepatitis A vaccines) have so far been administered parenterally.

Thus, in certain embodiments, the immunogenic formulations may be administered orally (including buccally, sublingually and by gastric lavage or other artificial feeding means). Such oral delivery may be accomplished using solid or liquid formulations, for example in the form of tablets, capsules, multi-particulates, gels, films, ovules, elixirs, solutions, suspensions, etc. In certain embodiments, when using a liquid formulation, the formulation may be administered in conjunction with a basic formulation (e.g., a bicarbonate solution) in order to neutralize the stomach pH. In certain embodiments, the basic formulation may be administered before and/or after the immunogenic formulation. In certain embodiments, the basic formulation may be combined with the immunogenic formulation prior to administration or taken at the same time as the immunogenic formulation.

While oral delivery is of particular interest, it will be appreciated that in certain embodiments, an immunogenic formulation may also be formulated for delivery parenterally, e.g., by injection. In such embodiments, administration may be, for example, intravenous, intramuscular, intradermal, or subcutaneous, or via by infusion or needleless injection techniques. For such parenteral administration, the immunogenic formulations may be prepared and maintained in conventional lyophilized formulations and reconstituted prior to administration with a pharmaceutically acceptable saline solution, such as a 0.9% saline solution. The pH of the injectable formulation can be adjusted, as is known in the art, with a pharmaceutically acceptable acid, such as methanesulfonic acid. Other acceptable vehicles and solvents that may be employed include Ringer's solution and U.S.P. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid formulations which can be dissolved or dispersed in sterile water or other sterile injectable medium prior to use.

The immunogenic formulations can also be administered intranasally or by inhalation and are conveniently delivered in the form of a dry powder inhaler or an aerosol spray presentation from a pressurized container, pump, spray, atomiser or nebuliser, with or without the use of a suitable propellant, e.g., dichlorodifluoromethane, trichlorofluoromethane, dichlorotetrafluoroethane, a hydrofluoroalkane, carbon dioxide or other suitable gas. In the case of a pressurized aerosol, the dosage unit may be determined by providing a valve to deliver a metered amount. The pressurized container, pump, spray, atomiser or nebuliser may contain a solution or suspension of the antibody, e.g., using a mixture of ethanol and the propellant as the solvent, which may additionally contain a lubricant, e.g., sorbitantrioleate. Capsules and cartridges (made, for example, from gelatin) for use in an inhaler or insufflator may be formulated to contain a powder mix of the immunogenic formulation and a suitable powder base such as lactose or starch.

Formulations for rectal administration are preferably suppositories which can be prepared by mixing the immunogenic formulation with suitable non-irritating excipients or carriers such as cocoa butter, polyethylene glycol or a suppository wax which are solid at ambient temperature but liquid at body temperature and therefore melt in the rectal vault and release the antibodies. Retention enemas and rectal catheters can also be used as is known in the art. Viscosity-enhancing carriers such as hydroxypropyl cellulose are also certain carriers of the disclosure for rectal administration since they facilitate retention of the formulation within the rectum. Generally, the volume of carrier that is added to the formulation is selected in order to maximize retention of the formulation. In particular, the volume should not be so large as to jeopardize retention of the administered formulation in the rectal vault.

Exemplary Formulations

In some embodiments, the present disclosure provides immunogenic formulations that include an antigen, a TLR-3 agonist adjuvant and a vesicle which comprises a non-ionic surfactant and a transport enhancer which facilitates the transport of lipid-like molecules across mucosal membranes. In some embodiments, these formulations may be administered orally. In some embodiments the TLR-3 agonist adjuvant comprises poly(I:C). In some embodiments the TLR-3 agonist adjuvant comprises poly(IC:LC). In some embodiments, the transport enhancer is a bile acid, a derivative thereof or a salt of any of these (e.g., sodium deoxycholate). In some embodiments, the non-ionic surfactant is a glycerol ester (e.g., 1-monopalmitoyl glycerol). In some embodiments, the vesicle further comprises an ionic amphiphile (e.g., dicetylphospate). In some embodiments, the vesicle further comprises a steroid (e.g., cholesterol). In some embodiments, the vesicles comprise 1-monopalmitoyl glycerol, dicetylphospate, cholesterol and sodium deoxycholate.

In some embodiments, the present disclosure provides immunogenic formulations that include an antigen, a TLR-3 agonist adjuvant and a vesicle which comprises a non-ionic surfactant. In some embodiments, these formulations may be administered parenterally (e.g., by intramuscular injection). In some embodiments the TLR-3 agonist adjuvant comprises poly(I:C). In some embodiments the TLR-3 agonist adjuvant comprises poly(IC:LC). In some embodiments, the non-ionic surfactant is a glycerol ester (e.g., 1-monopalmitoyl glycerol). In some embodiments, the vesicle further comprises an ionic amphiphile (e.g., dicetylphospate). In some embodiments, the vesicle further comprises a steroid (e.g., cholesterol). In some embodiments, the vesicles comprise 1-monopalmitoyl glycerol, dicetylphospate and cholesterol. In some embodiments, the vesicle may lack a transport enhancing molecule. In some embodiments, the vesicle may lack a "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, the vesicle may lack acyloxylated amino acids, such as acylcarnitines and salts thereof, and palmitoylcarnitines.

In some embodiments, the present disclosure provides immunogenic formulations that include an antigen, a TLR-4 agonist adjuvant and a vesicle which comprises a non-ionic surfactant and a transport enhancer which facilitates the transport of lipid-like molecules across mucosal membranes. In some embodiments, these formulations may be administered orally. In some embodiments the TLR-4 agonist adjuvant comprises monophosphoryl lipid A or 3-deacyl monophosphoryl lipid A. In some embodiments, the transport enhancer is a bile acid, a derivative thereof or a salt of any of these (e.g., sodium deoxycholate). In some embodiments, the non-ionic surfactant is a glycerol ester (e.g., 1-monopalmitoyl glycerol). In some embodiments, the vesicle further comprises an ionic amphiphile (e.g., dicetylphosphate). In some embodiments, the vesicle further comprises a steroid (e.g., cholesterol). In some embodiments, the vesicles comprise 1-monopalmitoyl glycerol, dicetylphospate, cholesterol and sodium deoxycholate.

In some embodiments, the present disclosure provides immunogenic formulations that include an antigen, a TLR-4 agonist adjuvant and a vesicle which comprises a non-ionic surfactant. In some embodiments, these formulations may be administered parenterally (e.g., by intramuscular injection). In some embodiments the TLR-4 agonist adjuvant comprises monophosphoryl lipid A or 3-deacyl monophosphoryl lipid A. In some embodiments, the non-ionic surfactant is a glycerol ester (e.g., 1-monopalmitoyl glycerol). In some embodiments, the vesicle further comprises an ionic amphiphile (e.g., dicetylphosphate). In some embodiments, the vesicle further comprises a steroid (e.g., cholesterol). In some embodiments, the vesicles comprise 1-monopalmitoyl glycerol, dicetylphospate and cholesterol. In some embodiments, the vesicle may lack a transport enhancing molecule. In some embodiments, the vesicle may lack a "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, the vesicle may lack acyloxylated amino acids, such as acylcarnitines and salts thereof, and palmitoylcarnitines.

In certain embodiments, formulations of the present disclosure comprise vesicles that display a lamellar structure (e.g., a bilayer structure). In some embodiments, formulations of the present disclosure are substantially lacking non-lamellar structures (e.g., micelles).

It will be appreciated that physical characteristics (e.g., lamellar structure) of vesicles present in formulations described herein may be measured by any known methods. For example, in some embodiments, physical characteristics of vesicles may be measured by $^{31}$P NMR at 25° C. In some embodiments, an anisotropic peak with a high field maximum at around −2.5 ppm with a chemical shift anisotropy of approximately 15 to 20 ppm is indicative of the presence of a lamellar structure. In some embodiments, an isotropic peak observed in $^{31}$P NMR spectra centered at around 2.5 ppm is indicative of the presence of non-lamellar structures. In some embodiments, the $^{31}$P NMR spectra of a formulation of the present disclosure is substantially lacking an isotropic peak at around 2.5 ppm. In some embodiments, if an isotropic peak at around 2.5 ppm is present then it has an intensity (peak height) that is less than the intensity (peak height) of an anisotropic peak with a chemical shift anisotropy of approximately 15 to 20 ppm and a high-field maximum at around −2.5 ppm. In some embodiments, if an isotropic peak at around 2.5 ppm is present then it has an intensity (peak height) that is less than 50% the intensity (peak height) of an anisotropic peak with a chemical shift anisotropy of approximately 15 to 20 ppm and a high-field maximum at around −2.5 ppm (e.g., less than 40%, less than 30%, less than 20%, less than 10%, less than 5%, less than 2% or less than 1%).

In some embodiments, the present disclosure provides any one of the aforementioned formulations in a lyophilized form.

III. Kits

In yet another aspect, the present disclosure provides kits that include a lyophilized lipid product in a first container and an aqueous solution comprising an antigen (and optionally an adjuvant) in a second container. In some embodiments, the kit also includes instructions for mixing the contents of the two containers in order to produce antigen-containing vesicle formulations.

As discussed above, the lyophilized lipid product is one that was previously prepared by melting vesicle-forming lipids to produce a molten lipid mixture and then lyophilizing the molten lipid mixture to produce the lyophilized lipid product.

In yet another aspect, the present disclosure provides kits that include any lyophilized antigen-containing vesicle formulation of the present disclosure in a first container and an aqueous solution (optionally containing an adjuvant) in a second container. In some embodiments, the kit also includes instructions for mixing the contents of the two containers in order to rehydrate the antigen-containing vesicle formulation.

In some embodiments, the kit may include additional components such as a syringe for injecting the antigen-containing vesicle formulation into a patient.

EXAMPLES

The following examples describe some exemplary modes of making and practicing certain formulations that are described herein. It should be understood that these examples are for illustrative purposes only and are not meant to limit the scope of the formulations and methods described herein.

Example 1: Three-Step Melt Method for Preparing Vesicles

This example describes a three-step melt method that was used to prepare some of the vesicles that are described in later examples.

In Step 1, a 5:4:1 molar ratio of the following lipids: 1-monopalmitoyl glycerol (MPG, 270 mg), cholesterol (CHO, 255 mg) and dicetyl phosphate (DCP, 90 mg) was placed in a flat bottom 50 ml glass beaker, ensuring none of the powder stuck to the side of the glassbeaker. The lipid mixture was then melted in a heated oil bath at 120° C. for 10 minutes, with occasional swirling in the glass beaker covered with aluminum foil.

While maintaining the temperature of the molten lipid mixture at 120° C., an emulsion was created in Step 2 by adding 10.9 ml of 25 mM bicarbonate buffer, pH 7.6 (preheated to 50° C.). The emulsion was immediately homogenized for 2 minutes at 50° C. (homogenization at 8000 rpm in 50° C. water bath). While still homogenizing, 1.1 ml of a 100 mM sodium deoxycholate (a "bile salt") solution in 25 mM bicarbonate buffer, pH 9.7 (preheated to 50° C.) was added and homogenization continued for 8 minutes at 50° C.

In Step 3, the antigen (e.g., HAV antigen or HBV surface antigen) in a PBS solution of approximately pH 7.2 was added to the heated molten lipid mixture containing the bile salt.

In a variation of this 3-step method, the molten lipid mixture prepared with bile salt in Step 2 was cooled to 30° C., incubated in an incubator/shaker (220 rpm) for 2 hours, frozen at −80° C., lyophilized and then reconstituted with the antigen solution in 100 mM phosphate buffer pH 8.5 prior to use.

Example 2: Inverted Two-Step Melt Method for Preparing Vesicles

This example describes an inverted two-step melt method that was used to prepare some of the vesicles that are described in later examples.

In Step 1, the same 5:4:1 molar ratio of lipids (MPG:CHO:DCP) was used; however, in this method, a 0.1-0.5 molar ratio of deoxycholic acid (a "bile acid") was also included and co-melted with the lipids in a heated oil bath at 135° C. for 10 minutes. In the method of Example 1, an aqueous bile salt solution was only added in Step 2 after converting the molten lipids into an emulsion.

At this stage, a stock solution of antigen (e.g., 4 ml of 25 μg/ml HAV antigen solution diluted with 6 ml of PBS buffer, pH 7.11 or 1.25 ml of 1.0 mg/ml HBV surface antigen solution diluted with 8.75 ml of PBS buffer, pH 7.2) was pre-incubated for 5 minutes in a heated water bath (25° C. to 50° C.). In Step 2, the resulting antigen stock solution was homogenized (at 8,000 rpm), the molten lipid mixture was added and homogenization continued for a further 10 minutes. The resulting homogenate was shaken for 2 hours at 220 rpm and 30° C. 10 ml of a 400 mM sucrose solution in PBS buffer was added to the shaken homogenate and the homogenate was further vortexed for 30 seconds. This mixture was frozen at −80° C., lyophilized and then reconstituted in 100 mM phosphate buffer pH 8.5 prior to use.

In a variation of this 2-step method, the co-melted lipid/bile acid solution prepared in Step 1 was cooled to 30° C., incubated in an incubator/shaker (220 rpm) for 2 hours, frozen at −80° C., lyophilized and then reconstituted with the antigen solution in 100 mM phosphate buffer pH 8.5 prior to use.

Example 3: Analysis of Hepatitis B Antigen Integrity

HBV surface antigen solutions were homogenized at 8,000 rpm at temperatures of 4° C., 25° C. and 50° C. Table 2 below compares the percent of resulting antigen measured by ELISA relative to un-manipulated antigen measured directly by ELISA. As shown, exposure of HBsAg to the 50° C. involved in the 3-step melt method of Example 1 destroyed more than 50% of the antigenic integrity of the antigen. Use of the inverted 2-step melt method of the present disclosure allows the temperature of the buffer containing antigen to be reduced substantially (e.g., to 25° C.). The inverted 2-step melt method, because it can utilize a lower temperature of antigen solution, allows for better preservation of subunit protein antigenicity.

TABLE 2

| Antigen | Temperature of Antigen Solution | | |
|---|---|---|---|
| | 4° C. | 25° C. | 50° C. |
| HBsAg | 67% | 71% | 38% |

Example 4: Analysis of Hepatitis B Antigen Entrapment

This example describes experiments that were performed in order to measure levels of hepatitis B surface antigen entrapment. Entrapment levels were measured using a Ninhydrin assay. The Ninhydrin assay is a colorimetric method of determining the concentration of a polypeptide in a sample. Substances containing amino groups react with the ninhydrin reagent to yield a blue-purple complex.

Hepatitis B surface antigen was entrapped in vesicles using the methods of Example 1 and 2. Two different ratios of bile acid (0.10 and 0.50) were tested using the method of Example 2. Entrapped hepatitis B surface antigens were hydrolyzed from the vesicles, neutralized, mixed with ninhydrin reagent and then incubated at 110° C. The solution was then allowed to cool and its absorbance was measured at 595 nm. There is a linear relationship between absorbance at this wavelength and the amount of polypeptide present in the original sample. Table 3 shows that high levels of antigen entrapment (in this case HBV surface antigen) were achieved using the inverted 2-step method of Example 2. Table 3 also suggests that entrapment efficiency may be affected by bile acid content.

TABLE 3

| Antigen | Vesicle Preparation Method | | |
|---|---|---|---|
| | 3-step melt | Inverted 2-step melt | |
| Bile salt/acid | 0.17 ratio of bile salt | 0.50 ratio of bile acid | 0.10 ratio of bile acid |
| HbsAg | 42% | 56% | 40% |

Example 5: Physiochemical Characterization of Vesicle Stability after Rehydration This example describes experiments that were performed in order to measure vesicle stability using dynamic light scattering. We determined particle size and size distribution using a Malvern Instrument Zetasizer Nano ZS (ZEN3600) using triplicate readings and a 2 minute equilibration time. 20 μl of vesicle sample was added to 980 μA of bicarbonate buffer pH 7.6, vortexed, and then added to a polystyrene cuvette (Sarstedt 67.754). Statistical analysis was performed using Minitab v14 with a 2-sample t-test at the 95% confidence level. The results obtained from the nano size analysis are shown in FIG. 1. Vesicles prepared as described in Examples 1 and 2 were measured using a mastersizer immediately after rehydration in the presence of buffer containing 2 μg of HAV antigen and at 2, 4 and 6 hours after rehydration. As shown in FIG. 1, vesicles prepared by the inverted 2-step melt method of Example 2 were more stable (as assessed by size stability) over time than vesicles prepared by the 3-step melt method of Example 1. Vesicle stability after hydration is a potentially important factor for vesicle formulations that will be administered to a patient.

Example 6: Antibody Response to Hepatitis a Antigen in Immunization of Mice

This Example describes in vivo testing of certain immunogenic formulations in mice. Vesicles were prepared as described in Examples 1 and 2 and then rehydrated in the presence of buffer containing 2 μg of HAV antigen. Female BALB/c mice (n=4) were vaccinated three times by oral gavage with these antigen-containing vesicles on days 0, 14, and 28 (equivalent to 2 μg HAV antigen/dose).

Figure 2:
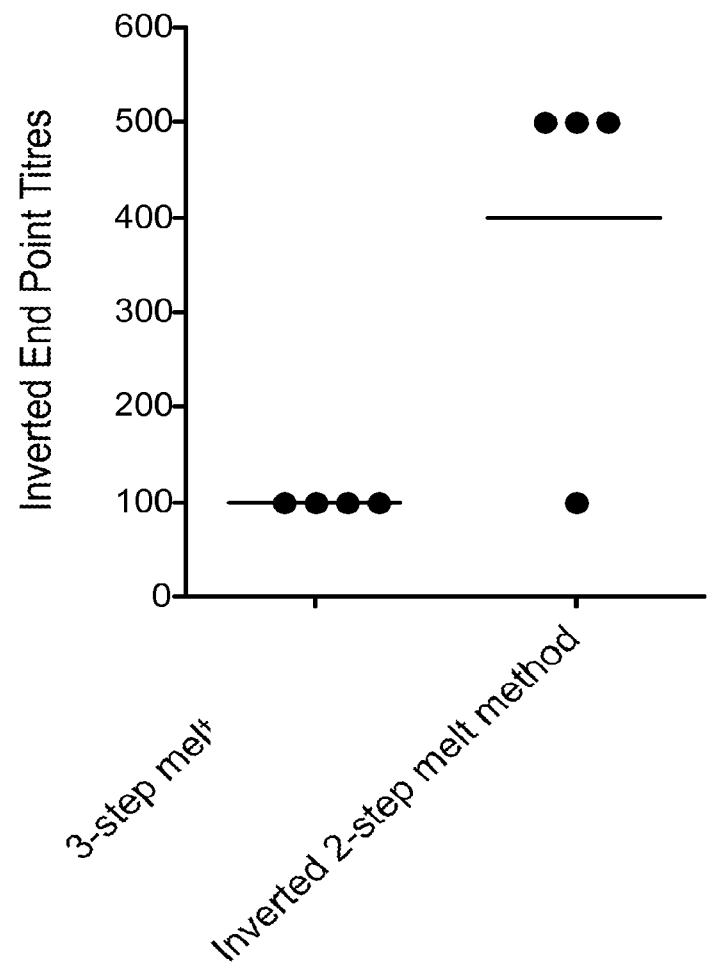
FIG. 2 shows the immune response caused by hepatitis A antigen-containing vesicles. Empty vesicles were prepared using the 3-step melt method of Example 1 and the inverted 2-step melt method of Example 2. Formulations were lyophilized and then rehydrated in the presence of buffer containing 2 µg of inactivated hepatitis A antigen. Mice were immunized orally 3 times on days 0, 14, and 28, and sera were tested for reactivity 14 days after the last vaccination. Each symbol represents that endpoint titer of scrum from an individual animal.

Serum samples were subsequently collected to assess hepatitis A-specific IgG titers induced by oral vaccination. Serum samples collected 14 days after the last immunization were tested by ELISA against inactivated HAV antigen. As shown in FIG. 2, oral vaccination of mice with vesicles prepared by the inverted 2-step melt method of Example 2 induced significantly higher systemic (serum) IgG responses against the hepatitis A antigen than vesicles prepared by the 3-step melt method of Example 1. Each symbol represents the endpoint titre of serum of an individual animal. This data demonstrates that hydration of empty vesicles prepared using the inverted 2-step melt method with HAV antigen results in better immunogenicity when compared to hydration of vesicles prepared using the 3-step melt method.

A number of researchers have demonstrated that currently licensed hepatitis A vaccines and hepatitis B vaccines given by intramuscular (IM) injection induce neutralizing IgG antibodies. We have found that orally administered immunogenic hepatitis A formulations are capable of inducing IgG antibodies systemically (serum samples) and IgA antibodies mucosally (nasal wash samples). Since hepatitis A and hepatitis B infection occurs via mucosal surfaces, an IgA response (the hallmark of a mucosal immune response) may be more efficacious than a systemic IgG response. We would only expect systemic IgG responses if the immunogenic hepatitis A or hepatitis B formulations were to be administered by standard parenteral routes (e.g., by IM injection).

Example 7: Bile Salt Content of Vesicles Affects Maturation of Immature Dendritic Cells It is now generally accepted that dendritic cells (DC) are important antigen presenting cells that play a role in establishing whether an antigen (for example HAV antigen) induces tolerance or a protective immune response in the intestine (Alpan et al., *J. Immunol.* 166 (8): 4843-4852, 2001). Activation of DCs, usually by inflammatory stimuli, promotes the expression of co-stimulatory molecules and presentation of antigens in a manner that allows productive priming of T cells.

Figure 3:
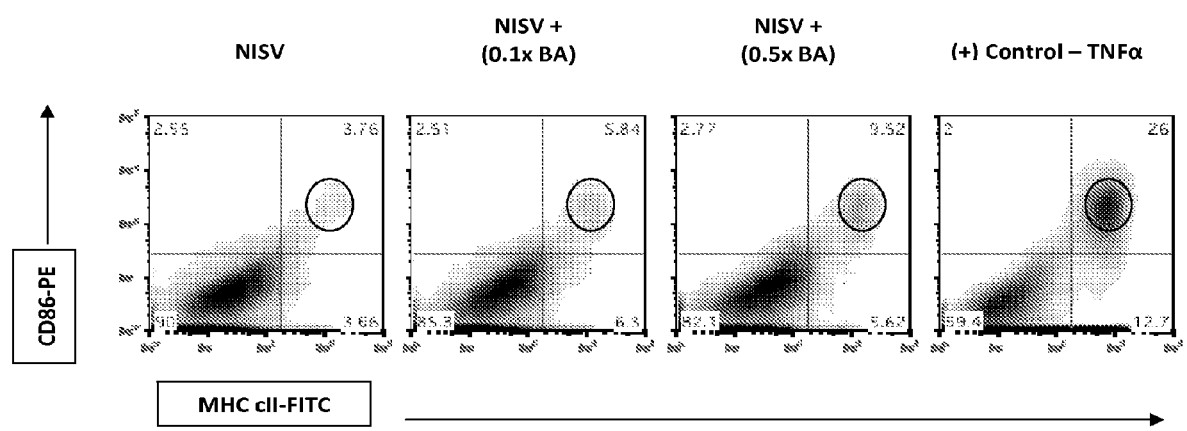
FIG. 3 shows that bile salt content in vesicles affects immature dendritic cell maturation as evidenced by flow cytometry. Maturation of immature dendritic cells was measured by flow cytometry using anti-MHC II and anti-CD86 antibodies. Mature DCs were defined as double positive for both antibodies. Immature dendritic cells were treated with non-ionic surfactant lipid vesicles (NISVs) prepared as in steps 1 and 2 of Example 2 (without the subsequent addition of antigen) and with or without two different molar ratios of bile acid to total lipid (0.1 and 0.5). As a positive control immature dendritic cells were treated with TNF-α alone.

Briefly, bone marrow derived DC progenitors were isolated from naïve BALB/c mice and cultured in the presence of interleukin 4 (IL-4) and granulocyte-macrophage colony stimulating factor (GM-CSF) which leads to differentiation to the immature DC phenotype (5 days). Subsequent treatment with tumor necrosis factor alpha (TNF-α) further differentiates immature DCs into mature dendritic cells. Immature DCs were incubated with non-ionic surfactant lipid vesicles (NISVs) prepared as in steps 1 and 2 of Example 2 (without the subsequent addition of antigen) with or without two different molar ratios of bile acid to total lipid (0.1 and 0.5). As a positive control immature DCs were treated with TNF-α alone. Maturation of DCs was measured by flow cytometry using anti-MHC II and anti-CD86 antibodies. Mature DCs were defined as double positive for both antibodies. As shown in FIG. 3, NISVs without bile acid did not significantly affect maturation of immature DCs while NISVs with bile acid increased maturation of DCs. The results also suggest that this increased maturation may be affected by bile acid content.

Example 8: Characterization of Vesicles by $^{31}$P NMR

This example describes the characterization by $^{31}$P NMR of certain exemplary vesicles that were prepared in accordance with the methods of the present disclosure.

Vesicles were prepared as described in Examples 1 and 2 without the addition of any antigen. Lyophilized vesicles were reconstituted in sodium bicarbonate (NaHCO$_3$) buffer. The final lipid concentration was 50 mg/ml. 4 ml of the suspended vesicles was transferred into a 10 mm NMR tube and a few drops of D$_2$O were added.

Figure 4:
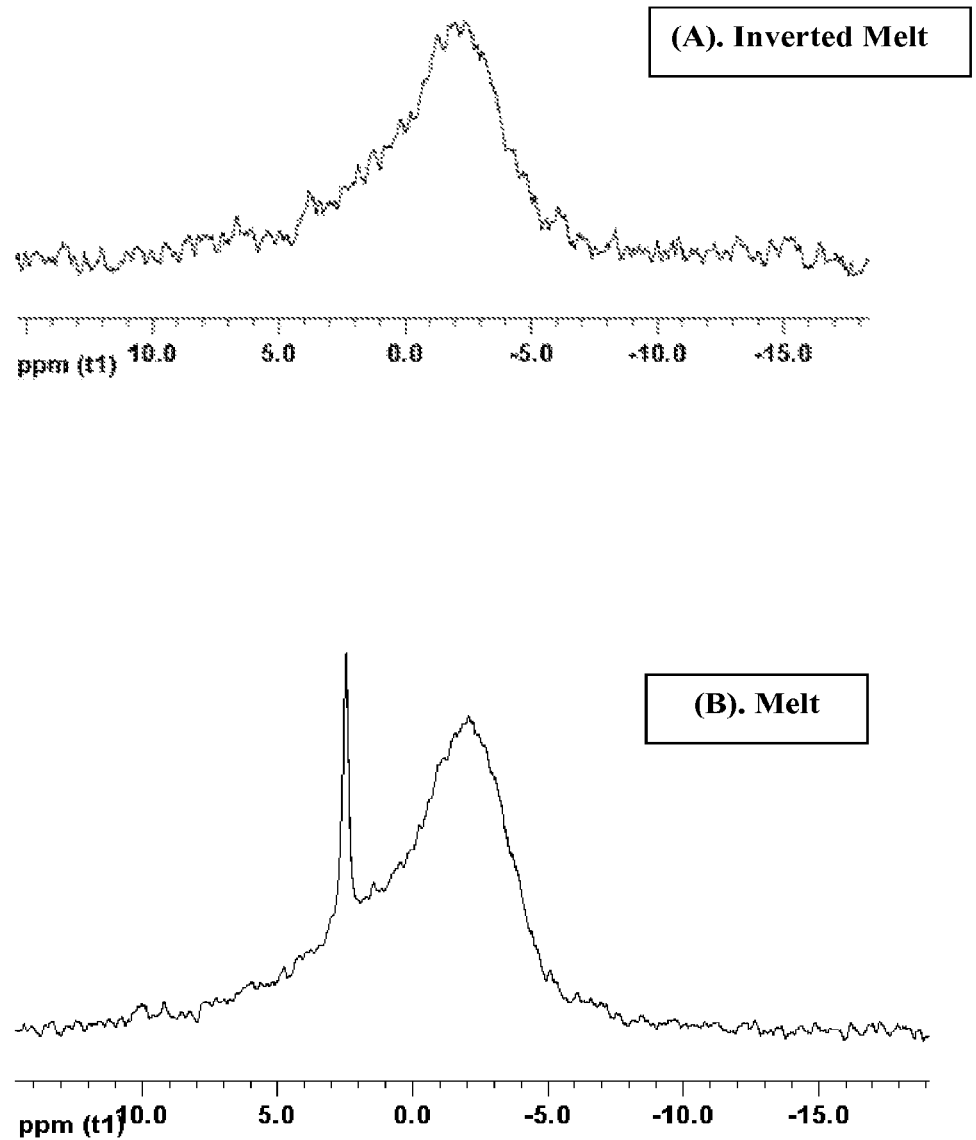
FIG. 4 compares the $^{31}$P NMR spectrum of exemplary vesicles prepared by the methods of Example 1 and 2 without the addition of any antigen. All spectra were collected at 25° C.

The $^{31}$P NMR spectrum of vesicles prepared using the inverted 2-step melt method is shown in FIG. 4A. The asymmetric line shape, with a low-field shoulder and a high-field peak and a chemical shift anisotropy of approximately 20 ppm corresponds to DCP organized in a typical lamellar structure.

The $^{31}$P NMR spectrum of vesicles prepared using the 3-step melt method is shown in FIG. 4B. An isotropic peak superimposed on the broad line and centered at around 2.5 ppm was observed in the samples prepared by this method. The isotropic peak may likely be attributed to the presence of the non-lamellar structures such as micelles, hexagonal phase, or vesicles of very small size (nanosize).

Example 9: Inverted Two-Step Melt Method for Preparing Vesicles

This example describes an exemplary inverted two-step melt method that may be used to prepare vesicles. A 5:4:1 molar ratio of lipids (5.575 g of MPG, 5.218 g of CHO, and 1.845 g of DCP) are placed in a flat bottom 250 mL glass beaker, ensuring none of the powder sticks to the side of the glass beaker. In certain embodiments, when bilosomes are made, bile acid is added at this step, e.g., a 0.5 molar ratio of deoxycholic acid (0.662 g of deoxycholic acid).

Using a clamp to hold the beaker containing lipids and bile acid, the beaker is covered with aluminum foil and lipids are allowed to melt in a heated oil bath at 140° C. to 145° C., with occasional swirling in the beaker.

At this stage, antigen stock solution is prepared by mixing antigen and concentrated Phosphate buffer (5.174 g of Na$_2$HPO$_4$ and 1.179 g of NaH$_2$PO$_4$ in 15 ml of WFI sterile water). The antigen stock solution is homogenized at 8000 rpm in a sterilized 1 L SS vessel. The melted lipids (with or without bile acid) are quickly transferred into the SS vessel via a sterilized glass funnel while continuing to homogenize the solution. The mixture is homogenized for 10 minutes at 8000 rpm. The resulting suspension is transferred into a 1 L sterile bottle and shaken for 1-2 hours at 220 rpm and 30° to 35° C.

In certain embodiments, the resulting suspension is split into two equal volumes (225 ml each) and the adjuvant Poly(IC:LC) is added as follows.

For the first group, Poly(IC:LC) in 400 mM sucrose solution is prepared by mixing 22.5 ml of a Poly(IC:LC) suspension (45 mg of Poly(IC:LC) at 2 mg/ml) and 202.5 ml of 400 mM sucrose solution in 100 mM Phosphate buffer. The resulting suspension is added to the first 225 ml volume of the antigen/vesicle suspension and shaken for 5 minutes at 220 rpm and 30° to 35° C.

For the second group, Poly(IC:LC) in 400 mM sucrose solution is prepared by mixing 7.5 ml of a Poly(IC:LC) suspension (15 mg of Poly(IC:LC) at 2 mg/ml) and 217.5 ml of 400 mM sucrose solution in 100 mM Phosphate buffer. The resulting suspension is added to the second 225 ml volume of the antigen/vesicle suspension and shaken for 5 minutes at 220 rpm and 30° to 35° C.

Samples may then be frozen at −80° C. overnight. In certain embodiments, samples are subsequently lyophilized and stored at 4° C.

Example 10: Inverted Two-Step Melt Method for Preparing Vesicles

This example describes another exemplary inverted two-step melt method that may be used to prepare vesicles. A 5:4:1 molar ratio of lipids (496 g of 1-monopalmitoyl glycerol (MPG), 496 g of cholesterol (CHO), and 164 g of dicetyl phosphate (DCP)) are placed in a flat bottom glass beaker, ensuring none of the powder sticks to the side of the glass beaker. A TLR-4 agonist is co-melted along with the lipids (e.g., 12 mg of PHAD™ (phosphorylated hexaacyl disaccharide from Avanti Polar Lipids)). The beaker is clamped and covered with aluminum foil and the lipids are melted in a heated oil bath at 120-125° C. with occasional swirling in the beaker.

At this stage, antigen stock solution is prepared by mixing antigen and a concentrated Phosphate buffer (5.980 g of $Na_2HPO_4$ and 1.363 g of $NaH_2PO_4$ in 20 ml of sterile water). The antigen stock solution is homogenized at 8,000 rpm at 30-35° C., and the melted lipids with TLR-4 agonist are quickly transferred into the beaker while homogenizing the solution. The mixture is homogenized at 8,000 rpm continued for 10 minutes at 30-35° C. The resulting lipid-antigen suspension is shaken for 1-2 hours at 220±10 rpm at 30-35° C.

In some embodiments, sucrose solution in water may be added to the vesicle/antigen solution and shaken for 5 minutes at 220±10 rpm at 30-35° C.

Samples may then be frozen at −80° C. overnight. In certain embodiments, samples are subsequently lyophilized and stored at 4° C.

INCORPORATION BY REFERENCE

The contents of any reference that is referred to herein are hereby incorporated by reference in their entirety.

Other Embodiments

It is intended that the specification and examples be considered as exemplary only. Other embodiments will be apparent to those skilled in the art from a consideration of the specification or practice of the methods, formulations and kits disclosed herein.

In particular, while the foregoing discussion has focused on the entrapment of antigens, it is to be understood that in general, the methods may be used to entrap any substance whether antigenic or non-antigenic. Therefore, in some embodiments, the methods of the present disclosure may be used to entrap one or more polypeptides, polynucleotides or polysaccharides that may or may not be antigenic. Specific classes of substances include, but are not limited to, adjuvants, enzymes, receptors, neurotransmitters, hormones, cytokines, cell response modifiers such as growth factors and chemotactic factors, antibodies, haptens, toxins, interferons, ribozymes, anti-sense agents, plasmids, DNA, and RNA. In some embodiments the polypeptide may be an antibody or antibody fragment, e.g., a humanized antibody. Table 4 provides a non-limiting list of exemplary substances that could be entrapped using the methods of the present disclosure.

TABLE 4

| Substance | Reference Drug |
|---|---|
| interferon gamma-1b | Actimmune ® |
| alteplase | Activase ®/Cathflo ® |
| antihemophilic factor | Advate |
| human albumin | Albutein ® |
| laronidase | Aldurazyme ® |
| interferon alfa-n3 | Alferon N ® |
| human antihemophilic factor | Alphanate ® |
| virus-filtered human coagulation factor IX | AlphaNine ® SD |
| alefacept | Amevive ® |
| bivalirudin | Angiomax ® |
| darbepoetin alfa | Aranesp ™ |
| bevacizumab | Avastin ™ |
| interferon beta-1a | Avonex ® |
| coagulation factor IX | BeneFix ™ |
| interferon beta-1b | Betaseron ® |
| tositumomab | Bexxar ® |
| antihemophilic factor | Bioclate ™ |
| human growth hormone | BioTropin ™ |
| botulinum toxin type A | Botox ® |
| alemtuzumab | Campath ® |
| acritumomab; technetium-99 labeled | CEA-Scan ® |
| alglucerase | Ceredase ® |
| imiglucerase | Cerezyme ® |
| crotalidae polyvalent immune Fab | CroFab ™ |
| digoxin immune Fab | DigiFab ™ |
| rasburicase | Elitek ® |
| etanercept | Enbrel ® |
| epoietin alfa | Epogen ® |
| cetuximab | Erbitux ™ |
| algasidase beta | Fabrazyme ® |
| urofollitropin | Fertinex ™ |
| follitropin beta | Follistim ™ |
| teriparatide | Forteo ® |
| human somatropin | GenoTropin ® |
| glucagon | GlucaGen ® |
| follitropin alfa | Gonal-F ® |
| antihemophilic factor | Helixate ® |
| factor XIII | Hemofil ® |
| insulin | Humalog ® |
| antihemophilic factor/von Willebrand factor complex-human | Humate-P ® |
| somatotropin | Humatrope ® |
| adalimumab | Humira ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| palifermin | Kepivance |
| anakinra | Kineret ™ |
| antihemophilic factor | Kogenate ® FS |
| insulin glargine | Lantus ® |
| granulocyte macrophage colony-stimulating factor | Leukine ® |
| lutropin alfa, for injection | Luveris |
| ranibizumab | Lucentis ® |
| gemtuzumab ozogamicin | Mylotarg ™ |
| galsulfase | Naglazyme ™ |
| nesiritide | Natrecor ® |
| pegfilgrastim | Neulasta ™ |
| oprelvekin | Neumega ® |
| filgrastim | Neupogen ® |
| fanolesomab | NeutroSpec ™ |
| somatropin | Norditropin ®/Norditropin Nordiflex ® |
| insulin; zinc suspension | Novolin L ® |
| insulin; isophane suspension | Novolin N ® |
| insulin, regular | Novolin R ® |
| insulin | Novolin ® |
| coagulation factor VIIa | NovoSeven ® |
| somatropin | Nutropin ® |

TABLE 4-continued

| Substance | Reference Drug |
|---|---|
| immunoglobulin intravenous | Octagam ® |
| pegylated-L-asparaginase | Oncaspar ® |
| abatacept | Orencia ™ |
| muromomab-CD3 | Orthoclone OKT3 ® |
| human chorionic gonadotropin | Ovidrel ® |
| pegylated interferon alfa-2a | Pegasys ® |
| pegylated interferon alfa-2b | PEG-Intron ™ |
| abarelix | Plenaxis ™ |
| epoietin alfa | Procrit ® |
| aldesleukin | Proleukin, IL-2 ® |
| somatrem | Protropin ® |
| dornase alfa | Pulmozyme ® |
| efalizumab | Raptiva ™ |
| interferon beta-1a | Rebif ® |
| antihemophilic factor | Recombinate ® |
| rAHF/ntihemophilic factor | ReFacto ® |
| lepirudin | Refludan ® |
| infliximab | Remicade ® |
| abciximab | RcoPro ™ |
| reteplase | Retavase ™ |
| rituximab | Rituxan ™ |
| interferon alfa-2a | Roferon-A ® |
| somatropin | Saizen ® |
| synthetic porcine secretin | SecreFlo ™ |
| basiliximab | Simulect ® |
| eculizumab | Soliris ® |
| pegvisomant | Somavert ® |
| palivizumab | Synagis ™ |
| thyrotropin alfa | Thyrogen ® |
| tenecteplasc | TNKasc ™ |
| natalizumab | Tysabri ® |
| interferon alfa-n1 | Wellferon ® |
| drotrecogin alfa | Xigris ™ |
| omalizumab | Xolair ® |
| daclizumab | Zenapax ® |
| ibritumomab tiuxetan | Zevalin ™ |
| somatotropin | Zorbtive ™ (Serostim ®) |

In addition, while the methods of the present disclosure are thought to be particularly applicable to thermolabile substances that are sensitive to their chemical and/or physical environment (e.g., biological substances such as microbes, polypeptides, polynucleotides, polysaccharides, etc.) it is to be understood that in some embodiments, the methods may also be used to entrap more stable substances including traditional small molecule therapeutics.

What is claimed is:

1. A method of forming antigen-containing vesicles, the method comprising:
adding a molten mixture of 1-monopalmitoyl glycerol, cholesterol and dicetyl phosphate to an aqueous solution comprising an antigen, thereby forming antigen-containing vesicles, wherein the antigen-containing vesicles comprise an aqueous compartment enclosed by one or more lipid bilayers.

2. The method of claim 1, wherein the aqueous solution comprising an antigen is temperature controlled.

3. The method of claim 2, wherein the aqueous solution comprising an antigen is kept at a temperature of less than about 50° C. during the step of adding.

4. The method of claim 2, wherein the aqueous solution comprising an antigen is kept at a temperature of less than about 40° C. during the step of adding.

5. The method of claim 2, wherein the aqueous solution comprising an antigen is kept at a temperature of less than about 30° C. during the step of adding.

6. The method of claim 1, wherein the molten mixture further comprises a transport enhancer which facilitates the transport of lipids across mucosal membranes.

7. The method of claim 1, wherein the molten mixture does not comprise a transport enhancer which facilitates the transport of lipids across mucosal membranes.

8. The method of claim 1, wherein the aqueous solution further comprises a lyoprotectant.

9. The method of claim 8, wherein the lyoprotectant is sucrose.

10. The method of claim 1, wherein the antigen is a virus.

11. The method of claim 10, wherein the virus is an attenuated virus or an inactivated virus.

12. The method of claim 1, wherein the antigen is selected from the group consisting of a polypeptide, a polynucleotide, and a polysaccharide.

13. The method of claim 1, wherein the antigen is thermolabile.

14. The method of claim 1, further comprising a step of adding an adjuvant after the antigen-containing vesicles are formed.

15. The method of claim 14, wherein the adjuvant is a TLR-3 agonist.

16. The method of claim 15, wherein the TLR-3 agonist is added with a lyoprotectant.

17. The method of claim 1, wherein the molten mixture further comprises an adjuvant.

18. The method of claim 17, wherein the adjuvant is a TLR-4 agonist.

19. The method of claim 1, further comprising a step of lyophilizing the antigen-containing vesicles.

20. The method of claim 19, further comprising a step of rehydrating the antigen-containing vesicles after they have been lyophilized.

* * * * *